United States Patent
Fujimaru et al.

(10) Patent No.: US 9,062,140 B2
(45) Date of Patent: Jun. 23, 2015

(54) POLYACRYLIC ACID (SALT) WATER-ABSORBENT RESIN, PRODUCTION PROCESS THEREOF, AND ACRYLIC ACID USED IN POLYMERIZATION FOR PRODUCTION OF WATER-ABSORBENT RESIN

(75) Inventors: Hirotama Fujimaru, Himeji (JP); Kunihiko Ishizaki, Suita (JP); Sei Nakahara, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 158 days.

(21) Appl. No.: 11/883,929

(22) PCT Filed: Apr. 6, 2006

(86) PCT No.: PCT/JP2006/307796
§ 371 (c)(1),
(2), (4) Date: Aug. 8, 2007

(87) PCT Pub. No.: WO2006/109845
PCT Pub. Date: Oct. 19, 2006

(65) Prior Publication Data
US 2008/0119626 A1    May 22, 2008

(30) Foreign Application Priority Data

Apr. 7, 2005   (JP) ................. 2005-110960
Apr. 7, 2005   (JP) ................. 2005-111204

(51) Int. Cl.
| | | |
|---|---|---|
| C08F 20/06 | (2006.01) | |
| C08F 220/06 | (2006.01) | |
| A61L 15/60 | (2006.01) | |
| C08F 222/10 | (2006.01) | |
| C08K 5/01 | (2006.01) | |
| C08K 5/04 | (2006.01) | |

(52) U.S. Cl.
CPC ............. *C08F 220/06* (2013.01); *A61L 15/60* (2013.01); *C08F 222/1006* (2013.01); *C08K 5/01* (2013.01); *C08K 5/04* (2013.01); *C08F 20/06* (2013.01)

(58) Field of Classification Search
USPC .......... 525/329.7; 524/332, 832; 526/317.1, 526/348; 562/88
See application file for complete search history.

(56) References Cited

U.S. PATENT DOCUMENTS

| | | | |
|---|---|---|---|
| 625,488 A | 5/1899 | Auspitz | |
| 632,352 A | 9/1899 | Jones | |
| 670,141 A | 3/1901 | Shepard | |
| 922,717 A | 5/1909 | Parker | |
| 955,086 A | 4/1910 | Laux | |
| 3,259,374 A | 7/1966 | Doebl et al. | |
| 3,346,242 A | 10/1967 | List | |
| 3,935,099 A | 1/1976 | Weaver et al. | |
| 3,959,569 A | 5/1976 | Burkholder, Jr. | |
| 4,043,952 A | 8/1977 | Ganslaw et al. | |
| 4,076,663 A | 2/1978 | Masuda et al. | |
| 4,090,013 A | 5/1978 | Ganslaw et al. | |
| 4,093,776 A | 6/1978 | Aoki et al. | |
| 4,124,748 A | 11/1978 | Fujimoto et al. | |
| 4,190,563 A | 2/1980 | Bosley et al. | |
| 4,224,427 A | 9/1980 | Mueller et al. | |
| 4,286,082 A | 8/1981 | Tsubakimoto et al. | |
| 4,320,040 A | 3/1982 | Fujita et al. | |
| 4,351,922 A | 9/1982 | Yoshida et al. | |
| 4,367,323 A | 1/1983 | Kitamura et al. | |
| 4,389,513 A | 6/1983 | Miyazaki et al. | |
| 4,416,711 A | 11/1983 | Jessop et al. | |
| 4,446,261 A | 5/1984 | Yamasaki et al. | |
| 4,455,284 A | 6/1984 | Sizyakov et al. | |
| 4,497,930 A | 2/1985 | Yamasaki et al. | |
| 4,526,937 A | 7/1985 | Hsu | |
| 4,558,091 A | 12/1985 | Hubbard | |

(Continued)

FOREIGN PATENT DOCUMENTS

| | | |
|---|---|---|
| CA | 2 433 044 A1 | 7/2002 |
| CA | 2 403 966 A1 | 9/2002 |

(Continued)

OTHER PUBLICATIONS

European Search Report dated Dec. 1, 2009 for coresponding European Patent Application No. 06731732.1.
Decision to Grant a Patent for an Invention, in corresponding Russian Application No. 2007140959, dated Aug. 14, 2009, with English translation.
Notice of Opposition dated Oct. 28, 2013 issued in European Application No. 06731728.9.
Ullmann's Encyclopedia of Industrial Chemistry (2003, Bd 33:S. 241-242, Bd.8:S. 247-248).
(2001) "Acrylic acid glacial, technical data sheet", *Industrial Organics, BASF*.
Office Action, dated Apr. 1, 2010 issued in U.S. Appl. No. 11/883,621.

(Continued)

*Primary Examiner* — Monique Peets
(74) *Attorney, Agent, or Firm* — Harness, Dickey & Pierce P.L.C.

(57) ABSTRACT

An embodiment of the present invention allows for the production, with a high productivity, of a water-absorbent resin having an improved relationship between absorption capacity and water-soluble polymer, which are conflicting properties of the water-absorbent resin, being easily controlled for polymerization reaction, being of no odor, being less colored, and being of high absorption properties (high absorption capacity under load and high PPUP). In one embodiment of the present invention, a process for producing a water-absorbent resin by polymerizing an acrylic acid composition including acrylic acid and/or its salt, the process includes: (a) the step of carrying out radical polymerization of the acrylic acid composition to form a hydrogel crosslinked polymer; and (b) the step of drying the hydrogel crosslinked polymer by application of heat, the acrylic acid composition having an unpolymerizable organic compound content of 1 to 1000 ppm by weight, wherein the unpolymerizable organic compound has a solubility parameter of $(1.0 \text{ to } 2.5) \times 10^4 (Jm^{-3})^{1/2}$.

10 Claims, No Drawings

(56) References Cited

U.S. PATENT DOCUMENTS

| | | |
|---|---|---|
| 4,587,308 A | 5/1986 | Makita et al. |
| 4,625,001 A | 11/1986 | Tsubakimoto et al. |
| 4,652,001 A | 3/1987 | Rathbun et al. |
| 4,654,039 A | 3/1987 | Brandt et al. |
| 4,666,983 A | 5/1987 | Tsubakimoto et al. |
| 4,683,274 A | 7/1987 | Nakamura et al. |
| 4,690,996 A | 9/1987 | Shih et al. |
| 4,693,713 A | 9/1987 | Chmelir et al. |
| 4,721,647 A | 1/1988 | Nakanishi et al. |
| 4,734,478 A | 3/1988 | Tsubakimoto et al. |
| RE32,649 E | 4/1988 | Brandt et al. |
| 4,738,867 A | 4/1988 | Itoh et al. |
| 4,748,076 A | 5/1988 | Saotome |
| 4,755,562 A | 7/1988 | Alexander et al. |
| 4,769,427 A | 9/1988 | Nowakowsky et al. |
| 4,771,105 A | 9/1988 | Shirai et al. |
| 4,783,510 A | 11/1988 | Saotome |
| 4,824,901 A | 4/1989 | Alexander et al. |
| 4,826,917 A | 5/1989 | Kondo et al. |
| 4,863,989 A | 9/1989 | Obayashi et al. |
| 4,873,299 A | 10/1989 | Nowakowsky et al. |
| 4,880,455 A | 11/1989 | Blank |
| 4,948,818 A | 8/1990 | Carmody et al. |
| 4,950,692 A | 8/1990 | Lewis et al. |
| 4,972,019 A | 11/1990 | Obayashi et al. |
| 4,973,632 A | 11/1990 | Nagasuna et al. |
| 4,985,514 A | 1/1991 | Kimura et al. |
| 4,985,518 A | 1/1991 | Alexander et al. |
| 5,002,986 A | 3/1991 | Fujiura et al. |
| 5,026,800 A | 6/1991 | Kimura et al. |
| 5,030,205 A | 7/1991 | Holdaway et al. |
| 5,051,259 A | 9/1991 | Olsen et al. |
| 5,061,259 A | 10/1991 | Goldman et al. |
| RE33,839 E | 3/1992 | Chmelir et al. |
| 5,124,416 A | 6/1992 | Haruna et al. |
| 5,140,076 A | 8/1992 | Hatsuda et al. |
| 5,145,906 A | 9/1992 | Chambers et al. |
| 5,147,343 A | 9/1992 | Kellenberger |
| 5,149,335 A | 9/1992 | Kellenberger et al. |
| 5,154,713 A | 10/1992 | Lind |
| 5,164,459 A | 11/1992 | Kimura et al. |
| 5,180,798 A | 1/1993 | Nakamura et al. |
| 5,185,413 A | 2/1993 | Yoshinaga et al. |
| 5,229,488 A | 7/1993 | Nagasuna et al. |
| 5,244,735 A | 9/1993 | Kimura et al. |
| 5,250,640 A | 10/1993 | Irie et al. |
| 5,264,495 A | 11/1993 | Irie et al. |
| 5,275,773 A | 1/1994 | Irie et al. |
| 5,288,814 A | 2/1994 | Long, II et al. |
| 5,296,650 A | 3/1994 | Kobayashi et al. |
| 5,300,192 A | 4/1994 | Hansen et al. |
| 5,308,896 A | 5/1994 | Hansen et al. |
| 5,314,420 A | 5/1994 | Smith et al. |
| 5,322,896 A | 6/1994 | Ueda et al. |
| 5,328,935 A | 7/1994 | Van Phan et al. |
| 5,338,766 A | 8/1994 | Phan et al. |
| 5,369,148 A | 11/1994 | Takahashi et al. |
| 5,371,148 A | 12/1994 | Taylor et al. |
| 5,380,808 A | 1/1995 | Sumiya et al. |
| 5,385,983 A | 1/1995 | Graham |
| 5,409,771 A | 4/1995 | Dahmen et al. |
| 5,419,956 A | 5/1995 | Roe |
| 5,422,405 A | 6/1995 | Dairoku et al. |
| 5,439,993 A | 8/1995 | Ito et al. |
| 5,447,727 A | 9/1995 | Graham |
| 5,447,977 A | 9/1995 | Hansen et al. |
| 5,453,323 A | 9/1995 | Chambers et al. |
| 5,455,284 A | 10/1995 | Dahmen et al. |
| 5,462,972 A | 10/1995 | Smith et al. |
| 5,475,062 A | 12/1995 | Ishizaki et al. |
| 5,478,879 A | 12/1995 | Kajikawa et al. |
| 5,506,324 A | 4/1996 | Gartner et al. |
| 5,532,323 A | 7/1996 | Yano et al. |
| 5,538,783 A | 7/1996 | Hansen et al. |
| 5,543,215 A | 8/1996 | Hansen et al. |
| 5,543,433 A | 8/1996 | Doetzer et al. |
| 5,562,646 A | 10/1996 | Goldman et al. |
| 5,571,618 A | 11/1996 | Hansen et al. |
| 5,574,121 A | 11/1996 | Irie et al. |
| 5,589,256 A | 12/1996 | Hansen et al. |
| 5,597,873 A | 1/1997 | Chambers et al. |
| 5,599,335 A | 2/1997 | Goldman et al. |
| 5,601,452 A | 2/1997 | Ruffa |
| 5,601,542 A | 2/1997 | Melius et al. |
| 5,609,727 A | 3/1997 | Hansen et al. |
| 5,610,208 A | 3/1997 | Dairoku et al. |
| 5,610,220 A | 3/1997 | Klimmek et al. |
| 5,614,570 A | 3/1997 | Hansen et al. |
| 5,624,967 A | 4/1997 | Hitomi et al. |
| 5,633,316 A | 5/1997 | Gartner et al. |
| 5,656,087 A | 8/1997 | Kikuchi et al. |
| 5,668,078 A | 9/1997 | Sumiya et al. |
| 5,669,894 A | 9/1997 | Goldman et al. |
| 5,672,633 A | 9/1997 | Brehm et al. |
| 5,684,072 A | 11/1997 | Rardon et al. |
| 5,712,316 A | 1/1998 | Dahmen et al. |
| 5,728,742 A | 3/1998 | Staples et al. |
| 5,744,564 A | 4/1998 | Stanley, Jr. et al. |
| 5,760,080 A | 6/1998 | Wada et al. |
| 5,795,893 A | 8/1998 | Bondinell et al. |
| 5,797,893 A | 8/1998 | Wada et al. |
| 5,801,238 A | 9/1998 | Tanaka et al. |
| 5,837,789 A | 11/1998 | Stockhausen et al. |
| 5,843,575 A | 12/1998 | Wang et al. |
| 5,849,405 A | 12/1998 | Wang et al. |
| 5,851,672 A | 12/1998 | Wang et al. |
| 5,853,867 A | 12/1998 | Harada et al. |
| 5,858,535 A | 1/1999 | Wang et al. |
| 5,861,429 A | 1/1999 | Sato et al. |
| 5,883,158 A | 3/1999 | Nambu et al. |
| 5,973,042 A | 10/1999 | Yoshinaga et al. |
| 5,981,070 A | 11/1999 | Ishizaki et al. |
| 5,985,944 A | 11/1999 | Ishizaki et al. |
| 5,987,070 A | 11/1999 | Fimoff et al. |
| 5,994,440 A | 11/1999 | Staples et al. |
| 6,037,431 A | 3/2000 | Shioji et al. |
| 6,054,541 A | 4/2000 | Wada et al. |
| 6,071,976 A | 6/2000 | Dairoku et al. |
| 6,076,277 A | 6/2000 | Eyerer et al. |
| 6,087,002 A | 7/2000 | Kimura et al. |
| 6,087,450 A | 7/2000 | Breitbach et al. |
| 6,099,950 A | 8/2000 | Wang et al. |
| 6,100,305 A | 8/2000 | Miyake et al. |
| 6,107,358 A | 8/2000 | Harada et al. |
| 6,110,992 A | 8/2000 | Wada et al. |
| 6,124,391 A | 9/2000 | Sun et al. |
| 6,127,454 A | 10/2000 | Wada et al. |
| 6,133,193 A | 10/2000 | Kajikawa et al. |
| 6,136,973 A | 10/2000 | Suzuki et al. |
| 6,140,395 A | 10/2000 | Hatsuda et al. |
| 6,143,821 A | 11/2000 | Houben |
| 6,150,582 A | 11/2000 | Wada et al. |
| RE37,021 E | 1/2001 | Aida |
| 6,174,929 B1 | 1/2001 | Hahnle et al. |
| 6,174,978 B1 | 1/2001 | Hatsuda et al. |
| 6,180,724 B1 | 1/2001 | Wada et al. |
| 6,184,433 B1 | 2/2001 | Harada et al. |
| 6,194,531 B1 | 2/2001 | Hatsuda et al. |
| 6,207,772 B1 | 3/2001 | Hatsuda et al. |
| 6,228,930 B1 | 5/2001 | Dairoku et al. |
| 6,232,520 B1 | 5/2001 | Hird et al. |
| 6,239,230 B1 | 5/2001 | Eckert et al. |
| 6,241,928 B1 | 6/2001 | Hatsuda et al. |
| 6,251,950 B1 | 6/2001 | Durden et al. |
| 6,251,960 B1 | 6/2001 | Ishizaki et al. |
| 6,254,990 B1 | 7/2001 | Ishizaki et al. |
| 6,284,362 B1 | 9/2001 | Takai et al. |
| 6,297,319 B1 | 10/2001 | Nagasuna et al. |
| 6,297,335 B1 | 10/2001 | Funk et al. |
| 6,300,275 B1 | 10/2001 | Weir |
| 6,300,423 B1 | 10/2001 | Engelhardt et al. |
| 6,310,156 B1 | 10/2001 | Maeda et al. |
| 6,313,231 B1 | 11/2001 | Hosokawa et al. |
| 6,323,252 B1 | 11/2001 | Gartner et al. |

(56) References Cited

U.S. PATENT DOCUMENTS

| | | |
|---|---|---|
| 6,335,406 B1 | 1/2002 | Nagasuna et al. |
| 6,360,077 B2 | 3/2002 | Mizoguchi |
| 6,372,852 B2 | 4/2002 | Hitomi et al. |
| 6,376,618 B1 | 4/2002 | Mitchell et al. |
| 6,388,000 B1 | 5/2002 | Irie et al. |
| 6,403,700 B1 | 6/2002 | Dahmen et al. |
| 6,414,214 B1 | 7/2002 | Engelhardt et al. |
| 6,417,425 B1 | 7/2002 | Whitmore et al. |
| 6,433,058 B1 | 8/2002 | Weir et al. |
| 6,444,744 B1 | 9/2002 | Fujimaru et al. |
| 6,448,320 B1 | 9/2002 | Igarashi et al. |
| 6,455,600 B1 | 9/2002 | Hahnle et al. |
| 6,458,921 B1 | 10/2002 | Dairoku et al. |
| 6,469,080 B2 | 10/2002 | Miyake et al. |
| 6,472,478 B1 | 10/2002 | Funk et al. |
| 6,514,615 B1 | 2/2003 | Sun et al. |
| 6,559,239 B1 | 5/2003 | Riegel et al. |
| 6,562,743 B1 | 5/2003 | Cook et al. |
| 6,562,879 B1 | 5/2003 | Hatsuda et al. |
| 6,565,768 B1 | 5/2003 | Dentler et al. |
| 6,579,958 B2 | 6/2003 | Wilson |
| 6,586,549 B1 | 7/2003 | Hatsuda et al. |
| 6,599,989 B2 | 7/2003 | Wada et al. |
| 6,605,673 B1 | 8/2003 | Mertens et al. |
| 6,620,889 B1 | 9/2003 | Mertens et al. |
| 6,620,899 B1 | 9/2003 | Morken et al. |
| 6,657,015 B1 | 12/2003 | Riegel et al. |
| 6,667,372 B1 | 12/2003 | Miyake et al. |
| RE38,444 E | 2/2004 | Wada et al. |
| 6,716,894 B2 | 4/2004 | Kajikawa et al. |
| 6,716,929 B2 | 4/2004 | Wilson |
| 6,720,073 B2 | 4/2004 | Lange et al. |
| 6,727,345 B2 | 4/2004 | Kajikawa et al. |
| 6,730,387 B2 | 5/2004 | Rezai et al. |
| 6,743,391 B2 | 6/2004 | Sun et al. |
| 6,787,001 B2 | 9/2004 | Sakamoto et al. |
| 6,809,158 B2 | 10/2004 | Ikeuchi et al. |
| 6,831,142 B2 | 12/2004 | Mertens et al. |
| 6,835,325 B1 | 12/2004 | Nakamura et al. |
| 6,841,229 B2 | 1/2005 | Sun et al. |
| 6,849,665 B2 | 2/2005 | Frenz et al. |
| 6,927,268 B2 | 8/2005 | Matsumoto et al. |
| 6,930,221 B1 | 8/2005 | Strandqvist |
| 6,951,895 B1 | 10/2005 | Qin et al. |
| 6,992,144 B2 | 1/2006 | Dairoku et al. |
| 7,049,366 B2 | 5/2006 | Nakahara et al. |
| 7,157,141 B2 | 1/2007 | Inger et al. |
| 7,169,843 B2 | 1/2007 | Smith et al. |
| 7,173,086 B2 | 2/2007 | Smith et al. |
| 7,179,875 B2 | 2/2007 | Fuchs et al. |
| 7,282,262 B2 | 10/2007 | Adachi et al. |
| 7,285,599 B2 | 10/2007 | Mertens et al. |
| 7,307,132 B2 | 12/2007 | Nestler et al. |
| 7,378,453 B2 | 5/2008 | Nogi et al. |
| 7,435,477 B2 | 10/2008 | Adachi et al. |
| 7,473,739 B2 | 1/2009 | Dairoku et al. |
| 7,510,988 B2 | 3/2009 | Wada et al. |
| 7,557,245 B2 | 7/2009 | Nordhoff et al. |
| 7,572,864 B2 | 8/2009 | Mertens et al. |
| 7,582,705 B2 | 9/2009 | Dairoku et al. |
| 7,745,537 B2 | 6/2010 | Nakashima et al. |
| 7,750,085 B2 | 7/2010 | Torii et al. |
| 7,803,880 B2 | 9/2010 | Torii et al. |
| 7,816,445 B2 | 10/2010 | Dairoku et al. |
| 7,851,550 B2 | 12/2010 | Kadonaga et al. |
| 7,879,923 B2 | 2/2011 | Matsumoto et al. |
| 7,960,469 B2 | 6/2011 | Adachi et al. |
| 8,198,209 B2 | 6/2012 | Torii et al. |
| 8,309,654 B2 | 11/2012 | Miyake et al. |
| 8,430,960 B2 | 4/2013 | Sumakeris et al. |
| 8,497,226 B2 | 7/2013 | Torii et al. |
| 8,552,134 B2 | 10/2013 | Fujimaru et al. |
| 8,596,931 B2 | 12/2013 | Nagashima et al. |
| 2001/0025093 A1 | 9/2001 | Ishizaki et al. |
| 2001/0046867 A1 | 11/2001 | Mizoguchi |
| 2001/0053807 A1 | 12/2001 | Miyake et al. |
| 2001/0053826 A1 | 12/2001 | Hosokawa et al. |
| 2002/0013394 A1 | 1/2002 | Dairoku et al. |
| 2002/0040095 A1 | 4/2002 | Dairoku et al. |
| 2002/0072471 A1 | 6/2002 | Ikeuchi et al. |
| 2002/0120074 A1 | 8/2002 | Wada et al. |
| 2002/0120085 A1 | 8/2002 | Matsumoto et al. |
| 2002/0127166 A1 | 9/2002 | Bergeron et al. |
| 2002/0128618 A1 | 9/2002 | Frenz et al. |
| 2002/0161132 A1 | 10/2002 | Irie et al. |
| 2002/0165288 A1 | 11/2002 | Frenz et al. |
| 2002/0169252 A1 | 11/2002 | Wilson |
| 2002/0193492 A1 | 12/2002 | Wilson |
| 2003/0020199 A1 | 1/2003 | Kajikawa et al. |
| 2003/0060112 A1 | 3/2003 | Rezai et al. |
| 2003/0065215 A1 | 4/2003 | Sakamoto et al. |
| 2003/0069359 A1 | 4/2003 | Torii et al. |
| 2003/0092849 A1 | 5/2003 | Dairoku et al. |
| 2003/0100830 A1* | 5/2003 | Zhong et al. ............. 600/431 |
| 2003/0118820 A1 | 6/2003 | Sun et al. |
| 2003/0118821 A1 | 6/2003 | Sun et al. |
| 2003/0153887 A1 | 8/2003 | Nawata et al. |
| 2003/0207997 A1 | 11/2003 | Mertens et al. |
| 2004/0019342 A1 | 1/2004 | Nagasuna et al. |
| 2004/0024104 A1 | 2/2004 | Ota et al. |
| 2004/0042952 A1 | 3/2004 | Bergeron et al. |
| 2004/0050679 A1* | 3/2004 | Hammon et al. ............. 203/6 |
| 2004/0071966 A1 | 4/2004 | Inger et al. |
| 2004/0106745 A1 | 6/2004 | Nakashima et al. |
| 2004/0110006 A1 | 6/2004 | Ishizaki et al. |
| 2004/0110897 A1 | 6/2004 | Sakamoto et al. |
| 2004/0110913 A1 | 6/2004 | Kanto et al. |
| 2004/0110914 A1 | 6/2004 | Nakahara et al. |
| 2004/0157734 A1 | 8/2004 | Mertens et al. |
| 2004/0176544 A1 | 9/2004 | Mertens et al. |
| 2004/0180189 A1 | 9/2004 | Funk et al. |
| 2004/0181031 A1 | 9/2004 | Nogi et al. |
| 2004/0213892 A1 | 10/2004 | Jonas et al. |
| 2004/0236049 A1 | 11/2004 | Fuchs et al. |
| 2004/0242761 A1 | 12/2004 | Dairoku et al. |
| 2005/0000671 A1 | 1/2005 | Ishii et al. |
| 2005/0013865 A1 | 1/2005 | Nestler et al. |
| 2005/0020780 A1 | 1/2005 | Inger et al. |
| 2005/0048221 A1 | 3/2005 | Irie et al. |
| 2005/0049379 A1 | 3/2005 | Adachi et al. |
| 2005/0070071 A1 | 3/2005 | Henley et al. |
| 2005/0070671 A1 | 3/2005 | Torii et al. |
| 2005/0080194 A1 | 4/2005 | Satake et al. |
| 2005/0101680 A1 | 5/2005 | Sun et al. |
| 2005/0113542 A1 | 5/2005 | Irie et al. |
| 2005/0118423 A1 | 6/2005 | Adachi et al. |
| 2005/0154146 A1 | 7/2005 | Burgert |
| 2005/0176910 A1 | 8/2005 | Jaworek et al. |
| 2005/0209352 A1 | 9/2005 | Dairoku et al. |
| 2005/0209411 A1 | 9/2005 | Nestler et al. |
| 2005/0215734 A1 | 9/2005 | Dairoku et al. |
| 2005/0215752 A1 | 9/2005 | Popp et al. |
| 2005/0221980 A1 | 10/2005 | Adachi et al. |
| 2005/0222459 A1 | 10/2005 | Nordhoff et al. |
| 2005/0222547 A1 | 10/2005 | Beruda et al. |
| 2005/0234413 A1 | 10/2005 | Funk et al. |
| 2005/0256469 A1 | 11/2005 | Qin et al. |
| 2005/0272600 A1 | 12/2005 | Wada et al. |
| 2005/0288182 A1 | 12/2005 | Torii et al. |
| 2006/0020078 A1 | 1/2006 | Popp et al. |
| 2006/0025536 A1 | 2/2006 | Dairoku et al. |
| 2006/0036043 A1 | 2/2006 | Nestler et al. |
| 2006/0073969 A1 | 4/2006 | Torii et al. |
| 2006/0074160 A1 | 4/2006 | Handa et al. |
| 2006/0079630 A1 | 4/2006 | Himori et al. |
| 2006/0089512 A1 | 4/2006 | Bennett et al. |
| 2006/0204755 A1 | 9/2006 | Torii et al. |
| 2006/0229413 A1 | 10/2006 | Torii et al. |
| 2007/0078231 A1 | 4/2007 | Shibata et al. |
| 2007/0101939 A1 | 5/2007 | Sumakeris et al. |
| 2007/0106013 A1 | 5/2007 | Adachi et al. |
| 2007/0149691 A1 | 6/2007 | Ishizaki et al. |
| 2007/0149716 A1 | 6/2007 | Funk et al. |
| 2007/0203280 A1 | 8/2007 | Okochi |

(56) References Cited

U.S. PATENT DOCUMENTS

| | | |
|---|---|---|
| 2007/0207924 A1 | 9/2007 | Ikeuchi et al. |
| 2007/0225422 A1 | 9/2007 | Sakamoto et al. |
| 2007/0239124 A1 | 10/2007 | Handa et al. |
| 2007/0254177 A1 | 11/2007 | Smith et al. |
| 2008/0021131 A1 | 1/2008 | Mertens et al. |
| 2008/0032888 A1 | 2/2008 | Nakamura et al. |
| 2008/0119586 A1 | 5/2008 | Byerly et al. |
| 2008/0119626 A1 | 5/2008 | Fujimaru et al. |
| 2008/0125533 A1 | 5/2008 | Riegel et al. |
| 2008/0139693 A1 | 6/2008 | Ikeuchi et al. |
| 2008/0161512 A1 | 7/2008 | Kawano et al. |
| 2008/0166410 A1 | 7/2008 | Funk et al. |
| 2009/0036855 A1 | 2/2009 | Wada et al. |
| 2009/0186542 A1 | 7/2009 | Kondo et al. |
| 2009/0234314 A1 | 9/2009 | Nakamura et al. |
| 2009/0239966 A1 | 9/2009 | Matsumoto et al. |
| 2010/0119312 A1 | 5/2010 | Nagashima et al. |
| 2010/0160883 A1 | 6/2010 | Jonas et al. |
| 2011/0301560 A1 | 12/2011 | Fujimura et al. |
| 2012/0184670 A1 | 7/2012 | Kobayashi et al. |
| 2012/0298913 A1 | 11/2012 | Kondo et al. |

FOREIGN PATENT DOCUMENTS

| | | | |
|---|---|---|---|
| CA | 2 426 514 A1 | 3/2003 | |
| CA | 2 426 802 A1 | 4/2003 | |
| CN | 1181272 A | 5/1998 | |
| CN | 1204665 A | 1/1999 | |
| CN | 1344756 A | 4/2002 | |
| CN | 1610707 A | 4/2005 | |
| DE | 10221202 A1 | 7/2003 | |
| EP | 0 001 706 A1 | 5/1979 | |
| EP | 0 205 674 | 12/1986 | |
| EP | 0 304 319 A2 | 2/1989 | |
| EP | 0 339 461 A1 | 11/1989 | |
| EP | 0 349 240 A2 | 1/1990 | |
| EP | 0 450 923 A2 | 10/1991 | |
| EP | 0 456 136 A2 | 11/1991 | |
| EP | 0 461 613 A1 | 12/1991 | |
| EP | 0 481 443 A1 | 4/1992 | |
| EP | 0 493 011 A2 | 7/1992 | |
| EP | 0 521 355 A1 | 1/1993 | |
| EP | 0 530 517 A1 | 3/1993 | |
| EP | 0 532 002 A1 | 3/1993 | |
| EP | 0 603 292 A1 | 6/1994 | |
| EP | 0 605 150 A1 | 7/1994 | |
| EP | 0 605 215 A1 | 7/1994 | |
| EP | 0 621 041 A1 | 10/1994 | |
| EP | 0 627 411 A1 | 12/1994 | |
| EP | 0 629 411 A1 | 12/1994 | |
| EP | 0 629 441 A1 | 12/1994 | |
| EP | 0 668 080 A2 | 8/1995 | |
| EP | 0 695 763 A1 | 2/1996 | |
| EP | 0 707 603 A1 | 4/1996 | |
| EP | 0 712 659 A1 | 5/1996 | |
| EP | 0 761 241 A2 | 3/1997 | |
| EP | 0 811 636 A1 | 12/1997 | |
| EP | 0 837 076 A2 | 4/1998 | |
| EP | 0 844 270 A1 | 5/1998 | |
| EP | 0 889 063 A1 | 1/1999 | |
| EP | 0 922 717 A1 | 6/1999 | |
| EP | 0 937 739 A2 | 8/1999 | |
| EP | 0 940 148 A1 | 9/1999 | |
| EP | 0942014 A2 | 9/1999 | |
| EP | 0 955 086 A2 | 11/1999 | |
| EP | 1 029 886 A2 | 8/2000 | |
| EP | 1 072 630 A1 | 1/2001 | |
| EP | 1 113 037 A2 | 7/2001 | |
| EP | 1 130 045 A2 | 9/2001 | |
| EP | 1 153 656 A2 | 11/2001 | |
| EP | 1 169 379 A1 | 1/2002 | |
| EP | 1 178 059 A2 | 2/2002 | |
| EP | 1 302 485 | 4/2003 | |
| EP | 1 315 770 A1 | 6/2003 | |
| EP | 1 364 985 A1 | 11/2003 | |
| EP | 1374919 A2 | 1/2004 | |
| EP | 1 457 541 | 9/2004 | |
| EP | 1 462 473 A1 | 9/2004 | |
| EP | 1 510 229 A1 | 3/2005 | |
| EP | 1 516 884 A2 | 3/2005 | |
| EP | 1577349 A1 | 9/2005 | |
| EP | 1 589 040 A1 | 10/2005 | |
| EP | 1598392 A2 | 11/2005 | |
| EP | 1 801 128 A2 | 6/2007 | |
| EP | 2 135 669 A1 | 12/2009 | |
| GB | 0 235 307 A | 6/1925 | |
| GB | 2 267 094 A | 11/1993 | |
| JP | 53-046389 B2 | 4/1978 | |
| JP | 54-037188 | 3/1979 | |
| JP | 55-038863 | 3/1980 | |
| JP | 55-133413 | 10/1980 | |
| JP | 56-133028 | 10/1981 | |
| JP | 56-136808 | 10/1981 | |
| JP | GB2088392 | * 11/1981 | ................ G08F 2/32 |
| JP | 57-073007 | 5/1982 | |
| JP | 57-094011 | 6/1982 | |
| JP | 57-158209 | 9/1982 | |
| JP | 58-501107 | 7/1983 | |
| JP | 58-180233 | 10/1983 | |
| JP | 59-062665 | 4/1984 | |
| JP | 59-080459 | 5/1984 | |
| JP | 59-129232 | 7/1984 | |
| JP | 60-055002 | 3/1985 | |
| JP | 60-071623 | 4/1985 | |
| JP | 60-158861 | 8/1985 | |
| JP | 60-163956 | 8/1985 | |
| JP | 60-245608 | 12/1985 | |
| JP | 61-016903 | 1/1986 | |
| JP | 61-046241 | 3/1986 | |
| JP | 61-087702 | 5/1986 | |
| JP | 61-97333 | 5/1986 | |
| JP | 61-257235 | 11/1986 | |
| JP | 62-007745 | 1/1987 | |
| JP | 62-227904 | 10/1987 | |
| JP | 62-270607 | 11/1987 | |
| JP | 63-105064 | 5/1988 | |
| JP | 63-270741 | 11/1988 | |
| JP | 63-297408 | 12/1988 | |
| JP | 64-056707 | 3/1989 | |
| JP | 01-126310 | 5/1989 | |
| JP | 01-126314 | 5/1989 | |
| JP | 02-049002 | 2/1990 | |
| JP | 02-191604 | 7/1990 | |
| JP | 02-196802 A | 8/1990 | |
| JP | 02-255804 | 10/1990 | |
| JP | 02-300210 | 12/1990 | |
| JP | 03-031306 | 2/1991 | |
| JP | 03-052903 | 3/1991 | |
| JP | 03-095204 | 4/1991 | |
| JP | 03-179008 | 5/1991 | |
| JP | 04-175319 B2 | 6/1992 | |
| JP | 04-227705 A | 8/1992 | |
| JP | 05-202199 B2 | 8/1993 | |
| JP | 05-508674 | 12/1993 | |
| JP | 06-041319 | 2/1994 | |
| JP | 06-039485 | 3/1994 | |
| JP | 06-057010 | 3/1994 | |
| JP | 06-080818 | 3/1994 | |
| JP | 06-107846 | 4/1994 | |
| JP | 06-122708 | 5/1994 | |
| JP | 06-158658 | 6/1994 | |
| JP | 06-199969 | 7/1994 | |
| JP | 06-211934 | 8/1994 | |
| JP | 06-220227 | 8/1994 | |
| JP | 06-262072 | 9/1994 | |
| JP | 07-008883 | 1/1995 | |
| JP | 07-145326 | 6/1995 | |
| JP | 07-145326 A | 6/1995 | |
| JP | 07-224204 | 8/1995 | |
| JP | 07-228788 | 8/1995 | |
| JP | 07-242709 | 9/1995 | |
| JP | 08-027278 | 1/1996 | |
| JP | 08-052203 | 2/1996 | |

(56) References Cited

FOREIGN PATENT DOCUMENTS

| | | |
|---|---|---|
| JP | 08-057311 | 3/1996 |
| JP | 08-143782 | 6/1996 |
| JP | 08-176311 | 7/1996 |
| JP | 08-188602 | 7/1996 |
| JP | 02-530668 B2 | 9/1996 |
| JP | 08-283318 | 10/1996 |
| JP | 09-077832 | 3/1997 |
| JP | 09-124710 | 5/1997 |
| JP | 09-124879 | 5/1997 |
| JP | 09-136966 | 5/1997 |
| JP | 09-235378 | 9/1997 |
| JP | 09-509591 | 9/1997 |
| JP | 09-278900 | 10/1997 |
| JP | 09-290000 | 11/1997 |
| JP | 10-045812 | 2/1998 |
| JP | 10-075999 | 3/1998 |
| JP | 10-114801 | 5/1998 |
| JP | 10-147724 | 6/1998 |
| JP | 10-273602 | 10/1998 |
| JP | 02-847113 B2 | 1/1999 |
| JP | 11-071425 | 3/1999 |
| JP | 11-071529 | 3/1999 |
| JP | 02-881739 B2 | 4/1999 |
| JP | 02-883330 B1 | 4/1999 |
| JP | 11-106514 | 4/1999 |
| JP | 11-240959 | 9/1999 |
| JP | 11-241030 | 9/1999 |
| JP | 11-254429 | 9/1999 |
| JP | 11-258229 | 9/1999 |
| JP | 11-302391 | 11/1999 |
| JP | 11-315147 | 11/1999 |
| JP | 02-995276 B2 | 12/1999 |
| JP | 2000-026738 A | 1/2000 |
| JP | 2000-053729 | 2/2000 |
| JP | 03-023203 B2 | 3/2000 |
| JP | 03-028203 B2 | 4/2000 |
| JP | 2000-093792 A | 4/2000 |
| JP | 2000-095965 A | 4/2000 |
| JP | 2000-290381 A | 10/2000 |
| JP | 2000-302876 A | 10/2000 |
| JP | 2000-327926 A | 11/2000 |
| JP | 03-115313 B2 | 12/2000 |
| JP | 2001-011341 A | 1/2001 |
| JP | 2001-040013 | 2/2001 |
| JP | 2001-040014 | 2/2001 |
| JP | 2001-096151 A | 4/2001 |
| JP | 2001-098170 A | 4/2001 |
| JP | 2001-137704 A | 5/2001 |
| JP | 2001-224959 A | 8/2001 |
| JP | 2001-226416 A | 8/2001 |
| JP | 2001-252307 A | 9/2001 |
| JP | 2001-523287 A | 11/2001 |
| JP | 2001-523289 A | 11/2001 |
| JP | 2002-035580 A | 2/2002 |
| JP | 2002-085959 A | 3/2002 |
| JP | 2002-121291 A | 4/2002 |
| JP | 03-283570 B2 | 5/2002 |
| JP | 2002-513043 A | 5/2002 |
| JP | 2002-513059 A | 5/2002 |
| JP | 2002-515079 A | 5/2002 |
| JP | 2002-212204 A | 7/2002 |
| JP | 2002-523526 A | 7/2002 |
| JP | 2002-241627 A | 8/2002 |
| JP | 2002-527547 A | 8/2002 |
| JP | 2002-265528 A | 9/2002 |
| JP | 2002-538275 A | 11/2002 |
| JP | 2002-539281 A | 11/2002 |
| JP | 2003-503554 A | 1/2003 |
| JP | 2003-062460 A | 3/2003 |
| JP | 2003-082250 A | 3/2003 |
| JP | 2003-088553 A | 3/2003 |
| JP | 2003-088554 A | 3/2003 |
| JP | 2003-511489 A | 3/2003 |
| JP | 2003-105092 A | 4/2003 |
| JP | 2003-516431 A | 5/2003 |
| JP | 2003-165883 A | 6/2003 |
| JP | 2003-206381 A | 7/2003 |
| JP | 2003-523484 A | 8/2003 |
| JP | 2003-246810 | 9/2003 |
| JP | 2003-261601 A | 9/2003 |
| JP | 2003-306609 A | 10/2003 |
| JP | 2003-529647 A | 10/2003 |
| JP | 2004-001355 A | 1/2004 |
| JP | 2004-002891 A | 1/2004 |
| JP | 03-501493 B2 | 3/2004 |
| JP | 2004-509196 A | 3/2004 |
| JP | 2004-121400 A | 4/2004 |
| JP | 2004-512165 A | 4/2004 |
| JP | 2004-210924 A | 7/2004 |
| JP | 2004-217911 A | 8/2004 |
| JP | 2004-261796 A | 9/2004 |
| JP | 2004-261797 A | 9/2004 |
| JP | 2004-300425 A | 10/2004 |
| JP | 2004-339678 A | 12/2004 |
| JP | 2004-352941 A | 12/2004 |
| JP | 2005-054050 | 3/2005 |
| JP | 2005-081204 A | 3/2005 |
| JP | 2005-097585 | 4/2005 |
| JP | 2005-105254 A | 4/2005 |
| JP | 2005-288265 A | 10/2005 |
| JP | 2006-008963 A | 1/2006 |
| JP | 2006-068731 A | 3/2006 |
| JP | 04-046617 B2 | 2/2008 |
| JP | 2008-523196 A | 7/2008 |
| JP | 2008-534695 | 8/2008 |
| JP | 04-214734 B2 | 1/2009 |
| JP | 2010-065107 A | 3/2010 |
| JP | 05-040780 B2 | 10/2012 |
| JP | 05-156034 B2 | 3/2013 |
| JP | 05-200068 B2 | 5/2013 |
| JP | 05-209022 B2 | 6/2013 |
| RU | 2 183 648 C2 | 6/2002 |
| RU | 2 193 045 C2 | 11/2002 |
| RU | 2106153 | 3/2010 |
| SU | 1777603 | 11/1992 |
| SU | 1797612 | 2/1993 |
| TW | 228528 | 8/1994 |
| TW | 396173 B | 7/2000 |
| TW | 399062 | 7/2000 |
| TW | 422866 | 2/2001 |
| TW | 432092 | 5/2001 |
| WO | WO-89/05327 A1 | 6/1989 |
| WO | WO-92/01008 A1 | 1/1992 |
| WO | WO-93/05080 A1 | 3/1993 |
| WO | WO-95/02002 A1 | 1/1995 |
| WO | WO-95/05856 A1 | 3/1995 |
| WO | WO-95/22355 A1 | 8/1995 |
| WO | WO-95/22356 A1 | 8/1995 |
| WO | WO-95/22358 A1 | 8/1995 |
| WO | WO-95/33558 A1 | 12/1995 |
| WO | WO-96/07437 A1 | 3/1996 |
| WO | WO-96/38296 A1 | 12/1996 |
| WO | WO-97/37695 A1 | 10/1997 |
| WO | WO-98/37149 A1 | 8/1998 |
| WO | WO-98/48857 A1 | 11/1998 |
| WO | WO-98/49221 A1 | 11/1998 |
| WO | WO 98/52979 | 11/1998 |
| WO | WO-99/55393 A1 | 11/1999 |
| WO | WO-99/55767 A1 | 11/1999 |
| WO | WO-00/10619 A1 | 3/2000 |
| WO | WO-00/38607 A1 | 7/2000 |
| WO | WO-00/53644 A1 | 9/2000 |
| WO | WO-00/53664 A1 | 9/2000 |
| WO | WO-00/55245 A1 | 9/2000 |
| WO | WO-01/45758 A1 | 6/2001 |
| WO | WO-01/66056 A1 | 9/2001 |
| WO | WO-01/68156 A1 | 9/2001 |
| WO | WO-01/68375 A2 | 9/2001 |
| WO | WO-01/74913 A1 | 10/2001 |
| WO | WO-01/89591 A2 | 11/2001 |
| WO | WO 01/98382 | 12/2001 |
| WO | WO-02/20068 A1 | 3/2002 |
| WO | WO-02/22717 A1 | 3/2002 |
| WO | WO-02/34384 A2 | 5/2002 |

(56) References Cited

FOREIGN PATENT DOCUMENTS

| WO | WO-02/053198 A1 | 7/2002 |
|---|---|---|
| WO | WO-02/053199 A1 | 7/2002 |
| WO | WO-02/100451 A2 | 12/2002 |
| WO | WO 03/014172 | 2/2003 |
| WO | WO-03/051415 A1 | 6/2003 |
| WO | WO 03/051940 | 6/2003 |
| WO | WO03/051940 * | 6/2003 |
| WO | WO-03078378 A1 | 9/2003 |
| WO | WO 03/095510 | 11/2003 |
| WO | WO-2004003036 A1 | 1/2004 |
| WO | WO-2004/018005 A1 | 3/2004 |
| WO | WO 2004/052819 | 6/2004 |
| WO | WO 2004/052949 | 6/2004 |
| WO | WO 2004/061010 | 7/2004 |
| WO | WO-2004/069293 A1 | 8/2004 |
| WO | WO-2004/069915 A2 | 8/2004 |
| WO | WO-2004/069936 A1 | 8/2004 |
| WO | WO-2004069404 A1 | 8/2004 |
| WO | WO-2004/113452 A1 | 12/2004 |
| WO | WO-2005/027986 A1 | 3/2005 |
| WO | WO-2005/075070 A1 | 8/2005 |
| WO | WO-2005/097313 A1 | 10/2005 |
| WO | WO-2006/062253 A1 | 6/2006 |
| WO | WO-2006/062258 A2 | 6/2006 |
| WO | WO-2006/063229 A2 | 6/2006 |
| WO | WO-2006/109844 A1 | 10/2006 |
| WO | WO-2006/109882 A1 | 10/2006 |
| WO | WO-2007/032565 A1 | 3/2007 |
| WO | WO-2007/037522 A1 | 4/2007 |
| WO | WO-2007/116777 A1 | 10/2007 |
| WO | WO-2008/015980 A1 | 2/2008 |
| WO | WO-2008/120742 A1 | 10/2008 |
| WO | WO-2009/048160 A1 | 4/2009 |
| WO | WO-2010/029074 A2 | 3/2010 |
| WO | WO-2010/073658 A1 | 7/2010 |

OTHER PUBLICATIONS

Office Action, dated Oct. 18, 2010 issued in U.S. Appl. No. 11/883,621.
Office Action, dated Mar. 18, 2011 issued in U.S. Appl. No. 11/883,621.
Office Action, dated Mar. 26, 2013 issued in U.S. Appl. No. 11/883,621.
Office Action, dated Jul. 11, 2012 issued in U.S. Appl. No. 11/883,621.
U.S. Appl. No. 11/883,621, filed Aug. 2, 2007.
Advisory Action dated Feb. 26, 2010 issued in U.S. Appl. No. 11/693,355.
Advisory Action dated Mar. 5, 2013 issued in U.S. Appl. No. 11/693,355.
Final rejection dated Nov. 27, 2009 issued in U.S. Appl. No. 11/693,355.
Final rejection dated Nov. 28, 2012 issued in U.S. Appl. No. 11/693,355.
Non-final rejection dated Aug. 1, 2012 issued in U.S. Appl. No. 11/693,355.
Non-final rejection dated Jun. 15, 2009 issued in U.S. Appl. No. 11/693,355.
Partial European Search Report dated Jun. 11, 2007 issued in European Application No. 07105112.2.
Office Action dated Apr. 1, 2014 issued in Japanese Application No. 2007-080101 with full English translation.
Office Action dated Apr. 4, 2014 issued in U.S. Appl. No. 13/498,780.
Office Action dated Mar. 21, 2014 issued in U.S. Appl. No. 11/723,822.
Supplementary European Search Report dated Jan. 17, 2014 issued in EP Application No. 10820587.3.
Korean Office Action together with its English translation.
The Polymer Handbook, 3rd Edition, p. 524 and p. 527-539.
Office Action dated Aug. 21, 2014 issued in U.S. Appl. No. 11/723,822.
http://www.home-water-purifiers-and-filters.com/carbon-water-filter.php (2011).
Office Action, dated Dec. 8, 2011 issued in U.S. Appl. No. 11/883,621.
State Intellectual Property Office of the P.R. China Examination Report.
Office Action dated Sep. 25, 2014 issued in U.S. Appl. No. 12/083,238.
US 6,863,978, 3/2005, Inger et al. (withdrawn).
"Chemicals Used for Treatment of Water", European Standard, EN 878, European Committee for Standardization, Jun. 2004.
"Solubility Parameter Values", The Polymer Handbook 3rd Edition, published by Wiley Interscience Publication, pp. 524, 525, 527-539.
A1: *Characterization Analysis* of the patent claims of EP 1 512 712 B1, Apr. 27, 2011.
A6: The step (B) and the step (D) are performed within 10 minutes in total, Möglichkeiten zu Merkmal.
Abstract of JP 06-211934 published on Aug. 2, 1994.
Abstract of JP 2000-026738 published on Jan. 25, 2000.
Belle Lowe (http://www.chestofbooks.com/food/science/Experimental-Cookery/Starch-Part-3.html). Book published 1943.
Buchholz et al., *Solution Polymerization*, Modern Superabsorbent Polymer Technology, p. 93, 1997.
*Chemistry/Engineering Handbook*, modified version No. 6, edited by Chemistry/Engineering Committee, Maruzen Co. 1999.
Chinese Office Action dated May 18, 2007 issued in Chinese Application No. 200510076831.8 with English translation.
Chinese Office Action dated Dec. 23, 2013 issued in Chinese Application No. 201210313591.9 with English translation.
Decision to Grant a Patent for an Invention dated Dec. 6, 2007 issued in Russian Application No. 2005140797/04(045428) with English translation.
Decision to Grant dated Aug. 14, 2009 issued in Russian Application No. 2007140959 with English translation.
Definition of "contain" from Merriam-Webster online dictionary, Apr. 2009.
Definition of "involve" from Merriam-Webster online dictionary, Apr. 2009.
European Office Action dated Dec. 2, 2005 issued in European Application No. 05013153.1.
European Search Report dated Aug. 1, 2007 issued in European Application No. 07005807.8.
European Search Report dated Jun. 11, 2007 issed in European Application No. 07005807.8.
European Search Report dated Nov. 26, 2007 issued in European Application No. 06026348.0.
European Search Report dated Jun. 3, 2008 issued in European Application No. 06026110.4.
Hammer mill (Technology), <http://de.wikipedia.org/wiki/Hammermühle_(Technik)>, printed Apr. 24, 2011.
Indian Office Action dated Jun. 9, 2011 issued in Indian Application No. 564/CHENP/2008.
International Search Report and International Preliminary Examination Report dated Oct. 12, 2004 issued in PCT Application No. PCT/JP2004/009242.
International Search Report dated Jan. 18, 2011 issued in Japanese Application No. PCT/JP2010/066957 with english translation.
International Search Report dated Apr. 25, 2006 issued in PCT Application No. PCT/JP2006/304895.
International Search Report dated Dec. 5, 2005 issued in PCT Application No. PCT/JP2005/018073.
International Search Report dated Sep. 5, 2006 issued in PCT Application No. PCT/JP2006/311637.
Japanese Office Action dated Jul. 10, 2012 in Japanese Application No. 2007-080101 with English Translation.
Japanese Office Action dated Apr. 23, 2013 issued in Japanese Application No. 2007-080101 with English translation.
Japanese Office Action dated Mar. 29, 2011 issued in Japanese Application No. 2005127818 with English translation.
Japanese Office Action dated Dec. 7, 2010 issued in Japanese Application No. 2005-127818 with English translation.

(56) References Cited

OTHER PUBLICATIONS

Kurimoto Powder System, *Continuous Kneading & Reacting System: KRC Kneader*, <http://www.kurimoto.co.jp/english/powdersystem/products/krc_Kneader.html>, printed Apr. 24, 2011.
Notice of Opposition dated Oct. 17, 2012 issued in EP Application No. 04773399.3 with English translation.
Notice of Opposition dated Apr. 28, 2011 issued in European Application No. 04021015.5 with English translation.
Notice of Opposition dated Oct. 28, 2013 issued in European Application No. 06731728.9 with English translation.
Office Action dated Jun. 1, 2006 issued in U.S. Appl. No. 10/933,319.
Office Action dated Jan. 10, 2011 issued in U.S. Appl. No. 12/805,685.
Office Action dated Aug. 14, 2013 issued in U.S. Appl. No. 13/498,780.
Office Action dated Dec. 14, 2012 issued in U.S. Appl. No. 11/723,822.
Office Action dated Jul. 14, 2009 issued in U.S. Appl. No. 11/723,822.
Office Action dated Jun. 14, 2010 issued in U.S. Appl. No. 10/562,140.
Office Action dated Mar. 14, 2007 issued in U.S. Appl. No. 10/562,140.
Office Action dated May 14, 2008 issued in U.S. Appl. No. 11/152,195.
Office Action dated Apr. 15, 2008 issued in U.S. Appl. No. 10/562,140.
Office Action dated Apr. 15, 2009 issued in U.S. Appl. No. 11/373,215.
Office Action dated Oct. 15, 2009 issued in U.S. Appl. No. 11/152,195.
Office Action dated Oct. 16, 2008 issued in U.S. Appl. No. 10/933,319.
Office Action dated Sep. 16, 2008 issued in U.S. Appl. No. 10/562,140.
Office Action dated Feb. 17, 2012 issued in U.S. Appl. No. 10/933,319.
Office Action dated Mar. 17, 2009 issued in U.S. Appl. No. 10/572,565.
Office Action dated Nov. 17, 2009 issued in U.S. Appl. No. 11/579,603.
Office Action dated Dec. 18, 2009 issued in U.S. Appl. No. 11/638,580.
Office Action dated Jun. 18, 2007 issued in U.S. Appl. No. 11/049,995.
Office Action dated Nov. 18, 2008 issued in U.S. Appl. No. 11/049,995.
Office Action dated Nov. 18, 2010 issued in U.S. Appl. No. 10/562,140.
Office Action dated Oct. 18, 2007 issued in U.S. Appl. No. 10/933,319.
Office Action dated Sep. 18, 2009 issued in U.S. Appl. No. 11/641,885.
Office Action dated Mar. 2, 2009 issued in U.S. Appl. No. 11/579,603.
Office Action dated Nov. 2, 2007 issued in U.S. Appl. No. 11/449,666.
Office Action dated Oct. 2, 2013 issued in U.S. Appl. No. 13/498,780.
Office Action dated Jul. 20, 2011 issued in U.S. Appl. No. 10/933,319.
Office Action dated Mar. 20, 2008 issued in U.S. Appl. No. 10/933,319.
Office Action dated Dec. 21, 2009 issued in U.S. Appl. No. 11/723,822.
Office Action dated Dec. 21, 2010 issued in U.S. Appl. No. 11/579,603.
Office Action dated Jan. 21, 2009 issued in U.S. Appl. No. 11/638,580.
Office Action dated Jun. 21, 2007 issued in U.S. Appl. No. 11/449,666.
Office Action dated May 21, 2010 issued in U.S. Appl. No. 11/638,580.
Office Action dated Mar. 22, 2010 issued in U.S. Appl. No. 11/641,885.
Office Action dated Oct. 22, 2013 issued in U.S. Appl. No. 11/723,822.
Office Action dated Dec. 23, 2013 issued in U.S. Appl. No. 12/083,238.
Office Action dated Oct. 23, 2006 issued in U.S. Appl. No. 10/933,319.
Office Action dated Sep. 23, 2011 issued in U.S. Appl. No. 12/083,238.
Office Action dated Dec. 24, 2008 issued in U.S. Appl. No. 11/373,215.
Office Action dated Jun. 26, 2009 issued in U.S. Appl. No. 11/638,580.
Office Action dated Aug. 28, 2012 issued in U.S. Appl. No. 12/805,685.
Office Action dated Feb. 28, 2007 issued in U.S. Appl. No. 10/933,319.
Office Action dated Oct. 28, 2008 issued in U.S. Appl. No. 11/152,195.
Office Action dated Oct. 28, 2009 issued in U.S. Appl. No. 10/572,565.
Office Action dated Sep. 28, 2007 issued in U.S. Appl. No. 10/562,140.
Office Action dated Apr. 30, 2007 issued in U.S. Appl. No. 11/449,666.
Office Action dated Apr. 30, 2009 issued in U.S. Appl. No. 11/579,603.
Office Action dated May 30, 2011 issued in U.S. Appl. No. 12/805,685.
Office Action dated Apr. 4, 2011 issued in U.S. Appl. No. 12/083,238.
Office Action dated Nov. 4, 2010 issued in U.S. Appl. No. 12/805,685.
Office Action dated Sep. 4, 2007 issued in U.S. Appl. No. 11/049,995.
Office Action dated Apr. 5, 2013 issued in U.S. Appl. No. 11/152,195.
Office Action dated May 7, 2009 issued in U.S. Appl. No. 11/152,195.
Office Action dated Jul. 8, 2010 issued in U.S. Appl. No. 11/579,603.
Office Action dated May 8, 2008 issued in U.S. Appl. No. 11/449,666.
Office Action dated May 8, 2013 issued in U.S. Appl. No. 11/723,822.
Office Action dated Feb. 9, 2009 issued in U.S. Appl. No. 10/562,140.
Partial European Search Report dated May 25, 2007 issued in European Application No. 06026348.0.
*Particle Size Analysis and Characterization of Classification Process: 6. Classification Methods*, Ullmann's Enc. Ind. Chem., 6th e.d. (2002) Electronic Release.
S. Kishi, "Handbook of Food Additives Edition 1981", Food and Science Company, pp. 285. (Partial English Translation).
S. Kishi: "Handbook of Food Additives Edition 1983", Food and Science Company, pp. 214, 217, 219, 221. (Partial English Translation).
Saxena (ftp://ftp.fao.org/es/esn/jecfa/cta/CTA_61_PVA.pdf) published 2004.
Taiwan Office Action dated Nov. 8, 2011 issued in Taiwanese Application No. 095147238 with English translation.
Ulshöfer et al., *Mathematical formula collection for secondary school*, Verlag Konrad Wittwer Stuggart, 3rd e.d., p. 4, 1988 (with English translation).
www.nichidene.com/Eng/kkh/b/b-2.htm.
Zschimmer & Schwarz (http://www.tandem-chemiscal.com/principles/zschimmer/ceramics_aux/special_info/E_PVAzubereitungen%5B1%5D.pdf) downloaded Dec. 4, 2009.
Chinese Office Action dated Jul. 17, 2009 issued in Chinese Application No. 200680011103.1 and English translation thereof.
Database WPI Week 200454, Thomson Scientific, London, GB, AN 2004-561593, XP0002555199.

(56) References Cited

OTHER PUBLICATIONS

European Office Action dated Dec. 2, 2009 issued in European Application No. 06731728.9-1214.

Pharmco Products Inc., Sodium Hydroxide 50% Product Specification Sheet (2002).

Korean Office Action dated Oct. 24, 2008 issued in Korean Patent Application No. 10-2007-7022676—with English translation.

State Intellectual Property Office of the P.R. China Examination Report dated Jan. 20, 2009 issued in Chinese Patent Application No. GCC/P/2006/6168.

A6: The step (B) and the step (D) are performed within 10 minutes in total, Möglichkeiten zu Merkmal, submitted to the European Patent Office on Apr. 28, 2011.

"Solubility Parameter Values", The Polymer Handbook $3^{rd}$ Edition, published by Wiley Interscience Publication (1989), pp. 524, 525, 527-539.

"Characteristic of Raw Starch", www.nichidene.com/Eng/kkh/b/b-2.htm accessed Jan. 6, 2009.

Database WPI Week 200454, Thomson Scientific, London, GB, AN 2004-561593, XP0002555199 accessed Nov. 26, 2009.

\* cited by examiner

POLYACRYLIC ACID (SALT) WATER-ABSORBENT RESIN, PRODUCTION PROCESS THEREOF, AND ACRYLIC ACID USED IN POLYMERIZATION FOR PRODUCTION OF WATER-ABSORBENT RESIN

TECHNICAL FIELD

The present invention relates to a polyacrylic acid (salt) water-absorbent resin, a production process thereof, and acrylic acid used in polymerization for production of water-absorbent resin. More specifically, the present invention particularly relates to (i) a water-absorbent resin having improved relationship between absorption capacity and water-soluble polymer, which are conflicting properties of the water-absorbent resin, (ii) a production process of the water-absorbent resin, and (iii) an acrylic acid for the production process of the absorbent resin.

BACKGROUND ART

In recent years, water-absorbent resins having a high water absorbency are developed and frequently used mainly for disposable uses, for example, as absorbent articles (e.g. disposable diapers and sanitary napkins) and further as water-retaining agents for agriculture and horticulture and for industrial sealing materials. As to such water-absorbent resins, many monomers and hydrophilic polymers are proposed as their raw materials. Of them, acrylic water-absorbent resins as obtained from acrylic acid and/or its salt as the monomers are industrially most commonly used because of their high water absorbency.

Because water-absorbent resins are generally used for disposable uses (such as disposable diapers), it is essential that they are inexpensive. Therefore, the enhancement of their productivity is in high demand. In addition, there is a natural high demand for the absorbent articles to avoid problems with respect to the safety and coloration of the absorbent articles. Specifically, the water-absorbent resin contains the unreacted residue of acrylic acid. Although the content of the unreacted acrylic acid is several hundred to about 1,000 ppm by weight, a decrease in the content of the unreacted acrylic acid is demanded. In addition, the water-absorbent resin is combined with white pulp in the absorbent articles. Therefore there is a high demand for the water-absorbent resin also to be white so as not to give any foreign-substance feeling or appearance caused by coloration.

In addition, the water-absorbent resin is water-swellable and water-insoluble. However, as described in Patent document 1, in the water-absorbent resin, there is also contained an uncrosslinked water-soluble polymer (water-soluble component) in the range of several wt % to several tens of wt %. The decrease of the content of this water-soluble component is also demanded. Moreover, as described in Patent document 2, the absorbent articles containing the water-absorbent resin is required to possess acceptable water absorption properties under pressure, such as absorption capacity under pressure and liquid permeability under pressure.

In order to solve the above problem, there has been suggested the process including the step of polymerizing a monomer having impurities in small amounts to produce a water-absorbent resin. Examples of such a process include: the process including the step of carrying out purification so that a monomer has a heavy metal content of not more than 0.1 ppm and the step of carrying out polymerization of the monomer (Patent document 3); the process including the step of carrying out polymerization by using acrylic acid including acrylic dimmer or oligomer in small amounts (Patent documents 4 and 5); the process including the step of carrying out purification of acrylic acid for polymerization to obtain an acetic acid or proprionic acid content of less than 400 ppm (Patent document 6); the process including the step of carrying out polymerization by using acrylic acid including protoanemonin in small amounts (Patent document 7); the process including the step of carrying out polymerization by using acrylic acid including furfural in small amounts (Patent document 8); and the process including the step of carrying out polymerization by using acrylic acid including hydroquinone in small amounts (Patent document 9). As the process including the step of reducing the amount of impurities in material for a water-absorbent resin, the following processes have been suggested. That is, the process including the step of treating acrylic acid with an aldehyde treatment agent (Patent document 10), and the process including the step of treating acrylate with an active carbon (Patent document 11).

As disclosed in Patent documents 3 through 11, there has been suggested the method for realizing a water-absorbent resin with excellent properties by the process including the step of purifying acrylic acid or the like as raw material at a high purity. However, there occurs the cost problem and the problem of decrease in productivity.

Furthermore, there has been suggested the polymerization process for a water-absorbent resin, including the step of adding trace components in certain amounts for the improvement in properties of the resulting water-absorbent resin. Examples thereof includes: the process in which acrylic acid has a methoxyphenol content of 10 to 200 ppm (Patent document 12); the process in which there coexists furfural of 11 to 2000 ppm (Patent document 13); and the process using metal (Patent documents 14 and 15). However, in Patent documents 12 and 13, there occurs the problem that the resultant water-absorbent resin becomes colored (turns yellow) due to oxidation of methoxyphenol and furfural, which are contained in a monomer, in the course of the production of a water-absorbent resin.

[Patent document 1]
U.S. Pat. No. 4,654,039
[Patent document 2]
U.S. Pat. No. 5,562,646
[Patent document 3]
Japanese Unexamined Patent Publication No. 31306/1991 (Tokukaihei 3-31306)
[Patent document 4]
Japanese Unexamined Patent Publication No. 211934/1994 (Tokukaihei 6-211934)
[Patent document 5]
International Publication WO04/52949
[Patent document 6]
International Publication WO03/95510
[Patent document 7]
European Patent No. 1302485
[Patent document 8]
U.S. Patent Application Publication No. 2004/0110913
[Patent document 9]
U.S. Pat. No. 6,444,744
[Patent document 10]
International Publication WO03/14172
[Patent document 11]
International Publication WO04/52819
[Patent document 12]
U.S. Patent Application Publication No. 2004/0110914
[Patent document 13]
U.S. Patent Application Publication No. 2004/0110897

[Patent document 14]
U.S. Pat. No. 5,439,993
[Patent document 15]
European Patent No. 1457541

DISCLOSURE OF INVENTION

An object of the present invention is to provide a process for producing a water-absorbent resin having an improved relationship between absorption capacity and water-soluble polymer, which are conflicting properties of a water-absorbent resin, being mildly controlled for polymerization reaction, maintaining and improving high absorption properties, being of no odor, being uncolored water-absorbent resin odor, and being produced with a high productivity.

In order to solve the problem, as a result of extensive research, the inventors of the present invention have found that the problem can be solved by producing a water-absorbent resin by an easy process including: the step of polymerizing a monomer including a particular unpolymerizable organic compound in a specified amount, the unpolymerizable organic compound having a solubility parameter of $(1.0$ to $2.5) \times 10^4 (Jm^{-3})^{1/2}$; and the step of carrying out a particular heat treatment, and have completed the present invention.

More specifically, in a process for producing a water-absorbent resin by polymerizing an acrylic acid composition including acrylic acid and/or its salt, the process includes: (a) the step of carrying out radical polymerization of the acrylic acid composition to form a hydrogel crosslinked polymer; and (b) the step of drying the hydrogel crosslinked polymer by application of heat, the acrylic acid composition having an unpolymerizable organic compound content of 1 to 1000 ppm by weight, wherein the unpolymerizable organic compound has a solubility parameter of $(1.0$ to $2.5) \times 10^4 (Jm^{-3})^{1/2}$.

In the process for obtaining a water-absorbent resin according to the present invention, the unpolymerizable organic compound is preferably included or added in advance in the acrylic acid composition. It is preferable that the acrylic acid composition is purified so that a content of the unpolymerizable organic compound included in the acrylic acid composition is adjusted to 1 to 1000 ppm by weight.

The unpolymerizable organic compound is at least one compound selected from the group consisting of heptane, dimethyl cyclohexane, ethyl cyclohexane, toluene, ethylbenzene, xylene, diethyl ketone, diisopropyl ketone, methyl propyl ketone, methyl isobutyl ketone, methyl-t-butyl ketone, n-propyl acetate, n-butyl acetate, diphenyl ether, and diphenyl. The unpolymerizable organic compound is aromatic compound.

The process for producing a water-absorbent resin of the present invention preferably further includes: after the step (b), (c) the step of subjecting the hydrogel crosslinked polymer to surface-crosslinking treatment by application of heat.

In the steps (b) and (c), the heat is preferably at a temperature not lower than a boiling point of the unpolymerizable organic compound. In the step (b), it is preferable to carry out hot-air drying with a gas having a dew point of 50 to 100° C.

In the process for producing a water-absorbent resin of the present invention, the acrylic acid composition preferably includes: methoxyphenol content of which is 10 to 200 ppm by weight; at least one compound content of which is 1 to 1000 ppm by weight, the compound being selected from the group consisting of β-hydroxypropionic acid and acrylic acid dimmer; and phenothiazine content of which is 0 to 0.1 ppm by weight. In the process for producing a water-absorbent resin of the present invention, the radical polymerization is preferably aqueous solution polymerization.

The process for producing a water-absorbent resin of the present invention is preferably such that the step (a) is a step of neutralizing the acrylic acid composition with a basic composition; and then carrying out radical polymerization of a resultant neutralized product, thereby forming a hydrogel crosslinked polymer, the basic composition including a basic compound and iron, the basic composition having an iron content of 0.2 to 5 ppm by weight in terms of $Fe_2O_3$.

A water-absorbent resin of the present invention is a water-absorbent resin produced by polymerizing the acrylic acid composition, the acrylic acid composition having an unpolymerizable organic compound content of not more than 10 ppm by weight and an iron content of 0.01 to 1 ppm by weight, wherein the unpolymerizable organic compound has a solubility parameter of $(1.0$ to $2.5) \times 10^4 (Jm^{-3})^{1/2}$.

The water-absorbent resin of the present invention is preferably such that the unpolymerizable organic compound is at least one compound selected from the group consisting of toluene, diphenyl ether, diphenyl, heptane, dimethyl cyclohexane, and ethyl cyclohexane.

A sanitary material of the present invention includes the water-absorbent resin of the present invention.

An acrylic acid composition of the present invention has an unpolymerizable organic compound content of 1 to 1000 ppm by weight, the unpolymerizable organic compound having a solubility parameter of $(1.0$ to $2.5) \times 10^4 (Jm^{-3})^{1/2}$.

A process for producing an acrylic acid composition of the present invention, includes: the step of purifying the acrylic acid composition in which an unpolymerizable organic compound having a solubility parameter of $(1.0$ to $2.5) \times 10^4 (Jm^{-3})^{1/2}$ is included or added in advance, so that a content of the unpolymerizable organic compound included in the acrylic acid composition is adjusted to 1 to 1000 ppm by weight.

Additional objects, features, and strengths of the present invention will be made clear by the description below.

BEST MODE FOR CARRYING OUT THE INVENTION

The following will describe the present invention in detail.
(1) Water-Absorbent Resin The "crosslinked water-absorbent resin" in the present invention refers to a polymer having water-swellability and water-insolubility as a result of introducing a crosslinked structure into the polymer, wherein the "water-swellability" means physiological saline absorbency (GVs) without pressure of at least 2 times, preferably 5 to 200 times, more preferably 20 to 100 times, and wherein the "water-insolubility" means substantial water-insolubility such that the water-soluble polymer content in the resin is essentially 0 to 50 wt %, preferably 0 to 25 wt %, more preferably 0 to 15 wt %, still more preferably 0 to 10 wt %. These properties are measured by methods defined in an example below.

A polyacrylic acid(salt) water-absorbent resin in the present invention is the one obtained by polymerizing a monomer including acrylic acid and/or its salt as a main component, wherein the acrylic acid and/or its salt is in a total amount of essentially 50 to 100 mol %, more preferably 70 to 100 mol %, still more preferably 90 to 100 mol %, particularly preferably substantially 100 mol %, relative to the entire monomers (exclusive of cross-linking agents) used for the polymerization. Note that, the term "monomer" herein refers to a monomer including acrylic acid and/or its salt as a main component, and is also used as a synonym for "acrylic acid component".

In terms of the properties, the acrylate used in the present invention is: preferably monovalent salts of acrylic acid, such as alkaline metal salts, ammonium salts, and amine salts; more preferably alkaline metal acrylates; and still more preferably alkaline metal acrylates selected from among sodium salt, lithium salt, and potassium salt. Further, polyvalent metal salts, such as calcium salts and aluminum salts, may be used in combination as long as the water-absorbent resin as obtained in the present invention has water-swellability.

The water-absorbent resin, as obtained in the present invention, is such that 20 to 99 mol %, preferably 50 to 95 mol %, more preferably 60 to 90 mol %, in terms of neutralization ratio, of the acid groups of the polymer are neutralized. The neutralization may be carried out either to the monomer component before polymerization, or to the hydrogel crosslinked polymer during and/or after polymerization. Furthermore, the neutralization of the monomer component and the neutralization of the polymer may be adopted in combination. However, it is preferable to subject acrylic acid as the monomer component, i.e. acrylic acid included in the acrylic acid composition, to alkali treatment as will be hereinafter described.

(2) Unpolymerizable Organic Compound

The unpolymerizable organic compound is an organic compound having no polymerizable unsaturated bond formed with a vinyl group, an allyl group, or the like, and the present invention uses, as an essential component, a monomer including an unpolymerizable organic compound content of 1 to 1000 ppm by weight, wherein the unpolymerizable organic compound has a solubility parameter of $(1.0 \text{ to } 2.5) \times 10^4 (Jm^{-3})^{1/2}$. In other words, the acrylic acid composition of the present invention include an unpolymerizable organic compound content of 1 to 1000 ppm by weight, wherein the unpolymerizable organic compound has a solubility parameter of $(1.0 \text{ to } 2.5) \times 10^4 (Jm^{-3})^{1/2}$. Note that, the unpolymerizable organic compound in the present invention is an organic compound with no polymerizable unsaturated bonds. Such an organic compound is (i) a compound having saturated bonds and being unpolymerizable by radical polymerization, ultraviolet polymerization, or gamma-ray polymerization by thermal decomposition or an oxidizing agent/reducing agent (aliphatic compound and alicyclic compound), or (ii) an organic compound such as an aromatic compound.

The solubility parameter ($\delta$) is herein a cohesive energy density and can be calculated from the following equation:

$$\delta((Jm^{-3})^{1/2}) = \rho \Sigma G/M \quad \text{(Equation 1)}$$

where $\rho$ is density (g/cm$^3$), G is the Holly cohesive energy constant, $\Sigma G$ is a sum of cohesive energy constants of component atom groups, $\rho$ and G are values at a temperature of 25±1° C., and M is molecular weight.

Herein, if the solubility parameter $\delta$ is calculated in the unit $((calm^{-3})^{1/2})$, the solubility parameter is appropriately expressed in the unit $(Jm^{-3})^{1/2}$.

For example, the value $\delta$ of solubility parameter specified in the publications such as The Polymer Handbook, 3rd Edition (pages 527 to 539; published by Wiley Interscience Publication) and Chemical handbook Basic Edition (published by the Chemical Society of Japan) is adopted. Also, as the solubility parameter of a solvent, which is not specified on the publications, the value $\delta$ which is obtained by substituting the Holly cohesive energy constant into the Small equation specified on page 524 of The Polymer Handbook is adopted.

The present invention uses the monomer including the above particular compound in certain amounts, thereby producing, with a high productivity, a water-absorbent resin having (i) an improved relationship between absorption capacity and water-soluble polymer, which are conflicting properties of the water-absorbent resin, (ii) being easily controlled for polymerization reaction, (iii) being less colored, and (iv) being of high absorption properties. A monomer having an unpolymerizable organic compound content of less than 1 ppm by weight, wherein the unpolymerizale organic compound has a solubility parameter of $(1.0 \text{ to } 2.5) \times 10^4 (Jm^{-3})^{1/2}$, is not preferred because it has the difficulty in being controlled for polymerization, which is caused by an excessive rise in temperature of a polymerized substance due to heat liberated by the polymerization, and causes degradation in absorption properties. Meanwhile, a monomer having an unpolymerizable organic compound content of more than 1000 ppm by weight, wherein the unpolymerizale organic compound has a solubility parameter of $(1.0 \text{ to } 2.5) \times 10^4 (Jm^{-3})^{1/2}$, includes too much amount of the unpolymerizable organic compound to achieve the object of the present invention, and might cause the problem, e.g. odor from a resultant water-absorbent resin.

Further, the particular compound (unpolymerizable organic compound) is finally removed by a particular heating step (e.g. drying and surface treatment) so that the resultant water-absorbent resin is free from odors and other problems.

Such an unpolymerizable organic compound is used in an amount of 1 to 1000 ppm by weight, preferably 1 to 500 ppm by weight, more preferably 1 to 300 ppm by weight, still more preferably 5 to 300 ppm by weight, particularly preferably, 10 to 300 ppm by weight, most preferably 10 to 100 ppm by weight, relative to the monomer (acrylic acid composition).

The solubility parameter of the unpolymerizable organic compound is essentially $(1.0 \text{ to } 2.5) \times 10^4 (Jm^{-3})^{1/2}$, preferably $(1.0 \text{ to } 2.2) \times 10^4 (Jm^{-3})^{1/2}$, more preferably $(1.1 \text{ to } 2.0) \times 10^4 (Jm^{-3})^{1/2}$, still more preferably $1.3 \text{ to } 2.0) \times 10^4 (Jm^{-3})^{1/2}$, and most preferably $(1.5 \text{ to } 1.9) \times 10^4 (Jm^{-3})^{1/2}$ The organic compound having a solubility parameter of $(1.0 \text{ to } 2.5) \times 10^4 (Jm^{-3})^{1/2}$, which is an organic compound having an excellent compatibility with acrylic acid and having no polymerizable unsaturated bonds, refers to a lipophilic organic compound. Of such unpolymerizable organic compounds, an organic compound having no halogen content is preferable, and hydrocarbon consisting of only carbon and hydrogen is more preferable, in terms of environmental loads. Further, a boiling point of the unpolymerizable organic compound is preferably 95 to 300° C., more preferably 130 to 260° C. The organic compound having a solubility parameter of more than $2.5 \times 10^4 (Jm^{-3})^{1/2}$ is not preferable in terms of polymerization control and polymerization reaction.

More specifically, the unpolymerizable organic compound is at least one compound selected from the group consisting of heptane (boiling point: 95° C.), dimethyl cyclohexane (boiling point: 132° C.), ethyl cyclohexane, toluene (boiling point: 110° C.), ethylbenzene (boiling point: 136° C.), xylene (boiling point: 138 to 144° C.), diethyl ketone (boiling point: 101° C.), diisopropyl ketone (boiling point: 124 to 125° C.), methyl propyl ketone (boiling point: 102° C.), methyl isobutyl ketone, methyl-t-butyl ketone, n-propyl acetate (boiling point: 101° C.), n-butyl acetate (boiling point: 124 to 125° C.), diphenyl ether (boiling point: 259° C.), and diphenyl (boiling point: 255° C.). Of these unpolymerizable organic compounds, preferably is at least one compound selected from the group consisting of heptane, ethylbenzene, xylene, methyl isobutyl ketone, methyl-t-butyl ketone, diphenyl ether, and diphenyl, more preferably hydrophobic compounds, still more preferably aromatic compounds, particularly preferably toluene, diphenyl ether, and diphenyl, most preferably toluene in terms of polymerization properties and productivity and further in terms of the effect of inhibiting oxidation and deterioration of a polymer chain after the completion of the polymerization step.

The unpolymerizable organic compound is essentially included in a monomer (acrylic acid composition) before polymerization. The monomer including unpolymerizable organic compound may be prepared in such a manner that the unpolymerizable organic compound is added to a monomer, i.e. acrylic acid composition after the preparation of the monomer, the unpolymerizable organic compound is added to a monomer i.e. acrylic acid composition during the preparation of the monomer, or the unpolymerizable organic compound is included in advance or added to raw materials for a monomer, i.e. components of acrylic acid composition including acrylic acid, cross-linking agents, water, and alkali compounds. In such preparation methods, the unpolymerizable organic compound is hydrophobic and generally water-insoluble, and therefore is preferably dissolved or included in acrylic acid, in advance. In the present invention, it is preferable that the unpolymerizable organic compound is included or added, in advance, to acrylic acid as used in preparing the monomer. That is, it is preferable that the unpolymerizable organic compound is dissolved in advance in an unneutralized acrylic acid so that the unneutralized acrylic acid is used for the preparation of an aqueous solution of the monomer.

The following will describe acrylic acid and acrylic acid composition as used in the present invention.

(3) Acrylic Acid and Acrylic Acid Composition

Examples of known industrial processes for producing acrylic acid include a process of catalytic gas phase oxidation of propylene and/or acrolein, an ethylene cyanohydrin process, a high pressure Reppe process, an improved Reppe process, a ketene process, and an acrylonitrile hydrolysis process. Of them, the process of catalytic gas phase oxidation of propylene and/or acrolein is most commonly employed. Then, in the present invention, acrylic acid as obtained by such a catalytic gas phase oxidation process is preferably used. This acrylic acid, as obtained by the catalytic gas phase oxidation process, usually contains impurities in an amount of not less than approximately 2000 ppm by weight. Such an acrylic acid including the impurities can be herein referred to as an acrylic acid composition.

In one of the processes for producing a water-absorbent resin according to the present invention, used is the acrylic acid composition preferably including the unpolymerizable organic compound of 1 to 1000 ppm by weight, in addition to acrylic acid. Preferably, the acrylic acid composition further includes β-hydroxypropionic acid and/or acrylic acid dimmer in total amounts of 1 to 1000 ppm by weight (based on the weight in terms of the unneutralized acrylic acid; hereinafter omitted), preferably 1 to 500 ppm by weight, more preferably 1 to 300 ppm by weight, and also includes methoxyphenol of 10 to 200 ppm by weight.

Specific examples of the aforementioned methoxyphenol include o-, m-, p-methoxyphenol and methoxyphenol which have at least one substituent such as methyl, t-butyl, or hydroxyl. In the present invention, p-methoxyphenol is particularly preferable. A methoxyphenol content is in the range of 10 to 200 ppm by weight, preferably in the range of 10 to 100 ppm by weight, more preferably in the range of 10 to 90 ppm by weight, still more preferably in the range of 10 to 80 ppm by weight, most preferably in the range of 10 to 70 ppm by weight. In the case where a p-methoxyphenol content is more than 200 ppm by weight, there occurs a problem that the resultant water-absorbent resin becomes colored (becomes tinged with yellow/turns yellow). On the other hand, in the case where the p-methoxyphenol content is less than 10 ppm by weight, particularly less than 5 ppm by weight, in other words, in the case where the p-methoxyphenol which is a polymerization inhibitor has been removed by purification such as distillation, not only is there a danger that the polymerization will take place before intentionally being initiated, but also, surprisingly, the polymerization rate rather becomes slow.

The (i) unpolymerizable organic compound and (ii) β-hydroxypropionic acid and/or acrylic acid dimmer included in total amounts of less than 1 ppm by weight make it difficult to control for polymerization, which is caused by an excessive rise in temperature of a polymerized substance due to heat liberated by the polymerization, and can cause degradation in absorption properties. The (i) unpolymerizable organic compound and (ii) β-hydroxypropionic acid and/or acrylic acid dimmer included in too much total amounts causes the increase of a residual monomer content (residual acrylic acid) in the water-absorbent resin.

Apart from the methoxyphenol, other polymerization inhibitors can be used in the acrylic acid composition as used in the present invention in the course of the production. For example, phenothiazine, hydroquinone, copper salts, and Methylene Blue are effective polymerization inhibitors. However, such polymerization inhibitors impair the polymerization, unlike the methoxyphenol. Such polymerization inhibitors in a lower content are desired, and the content of the polymerization inhibitors is preferably 0 to 0.1 ppm by weight, more preferably 0 ppm by weight (which is lower than a detection limit).

An acrylic acid composition as used in the present invention preferably has a protoanemonin and/or furfural content of 0 to 20 ppm by weight. As the protoanemonin and/or furfural content increases, not only does the polymerization time (time elapsed until the polymerization temperature reaches its peak) become longer to increase the residual monomer content, but also the water-soluble component content increases much more than the small increase in the absorption capacity, resulting in relative deterioration of properties. From the viewpoint of the enhancements of the properties and performances of the resultant water-absorbent resin, the protoanemonin and/or furfural content of the acrylic acid is more preferably not more than 10 ppm by weight, still more preferably in the range of 0.01 to 5 ppm by weight, yet still more preferably 0.05 to 2 ppm by weight, particularly preferably 0.1 to 1 ppm by weight.

Further, the acrylic acid composition as used in the present invention is preferably lower in aldehyde, except furfural, and/or maleic acid content. The aldehyde and/or maleic acid content is preferably 0 to 5 ppm by weight, more preferably 0 to 3 ppm by weight, still more preferably 0 to 1 ppm by weight, particularly preferably 0 ppm by weight (which is lower than a detection limit), relative to the weight of acrylic acid. Examples of aldehyde except furfural include benzoic aldehyde, acrolein, and acetaldehyde.

Still further, the acrylic acid composition as used in the present invention includes a saturated carboxylic acid composed of acetic acid and/or propionic acid. A saturated carboxylic acid content is preferably not more than 1000 ppm by weight, more preferably 10 to 800 ppm by weight, particularly preferably 100 to 500 ppm by weight, relative to the weight of acrylic acid. Such a saturated carboxylic acid is unpolymerizable and volatile. As such, the saturated carboxylic acid content of more than 1000 ppm by weight causes the odor problem. However, a low saturated carboxylic acid content is preferable because it causes the resultant water-absorbent resin to have a safe antibacterial activity.

In the present invention, examples of the process for obtaining the aforementioned acrylic acid composition, but are not limited to, include the following processes (A) to (D).

The quantification of the components included in the acrylic acid composition can be carried out by liquid chromatography or gas chromatography.

Process (A): A process including the step of distilling commercially available acrylic acid containing p-methoxyphenol as a polymerization inhibitor in an amount of 200 ppm by weight or an aqueous solution of this acrylic acid, thereby adjusting the contents of (i) an unpolymerizable organic compound having a solubility parameter of 1.0 to 2.5 $(Jcm^{-3})^{1/2}$ in the acrylic acid (boiling point: 139° C.), (ii) β-hydroxypropionic acid and/or acrylic acid dimmer, and (iii) methoxyphenol such as p-methoxyphenol (boiling point: 113 to 115° C./5 mmHg) to the above-specified contents.

Process (B): A process including the step of adding (i) an unpolymerizable organic compound having a solubility parameter of 1.0 to 2.5 $(Jcm^{-3})^{1/2}$ in the acrylic acid in an amount as defined in the present invention, (ii) β-hydroxypropionic acid and/or acrylic acid dimer, and (iii) methoxyphenol to methoxyphenol, such as p-methoxyphenol, as a polymerization inhibitor.

Process (C): A process including the step of adjusting (i) an unpolymerizable organic compound having a solubility parameter of 1.0 to 2.5 $(Jcm^{-3})^{1/2}$, (ii) β-hydroxypropionic acid and/or acrylic acid dimer, and (iii) methoxyphenol (p-methoxyphenol) to be in contents as respectively defined in the present invention, in a process for producing acrylic acid.

Process (D): A process including the step of blending acrylic acids having respectively different contents of unpolymerizable organic compound having a solubility parameter of $(1.0 \text{ to } 2.5) \times 10^4 (Jm^{-3})^{1/2}$, β-hydroxypropionic acid and/or acrylic acid dimmer, and methoxyphenol (e.g. p-methoxyphenol), thereby adjusting the contents of the unpolymerizable organic compound, the β-hydroxypropionic acid and/or acrylic acid dimmer, and methoxyphenol as those defined in the present invention.

Specific examples of processes for obtaining the acrylic acid composition (also referred to as acrylic acid including trace components as impurities) in the process (A), include processes involving distillation, crystallization, or adsorption by ion-exchange resins. Hereinafter, examples of the process involving the distillation and crystallization are described.

(1) A process including the steps of: distilling the commercially available acrylic acid with a distillation column having a condenser, a distillate-extracting tube, and a reflux-supplying tube at a top portion of the column and further having a boiler and a raw-material-liquid-supplying tube at a lower portion of the column and still further having a stabilizing-agent-supplying tube at an upper portion of the condenser; and, while adding an unpolymerizable organic compound having a solubility parameter of $(1.0 \text{ to } 2.5) \times 10^4 (Jm^{-3})^{1/2}$, β-hydroxypropionic acid and/or acrylic acid dimmer, and methoxyphenol from the stabilizing-agent-supplying tube, obtaining the acrylic acid composition having the unpolymerizable organic compound having a solubility parameter of $(1.0 \text{ to } 2.5) \times 10^4 (Jm^{-3})^{1/2}$, the β-hydroxypropionic acid and/or the acrylic acid dimmer, and the methoxyphenol respectively adjusted in predetermined amounts.

(2) A process including the step of introducing the commercially available acrylic acid into a crystallizer for its purification, thereby obtaining the acrylic acid having the unpolymerizable organic compound having a solubility parameter of $(1.0 \text{ to } 2.5) \times 10^4 (Jm^{-3})^{1/2}$, the β-hydroxypropionic acid and/or the acrylic acid dimmer, and the methoxyphenol in respectively specified amounts.

(3) A process including the step of purifying the acrylic acid composition so that the content of the unpolymerizable organic compound included in the acrylic acid composition is adjusted to 1 to 1000 ppm by weight. That is, a process including the step of preparing an acrylic acid composition by purifying acrylic acid having the unpolymerizable organic compound having a solubility parameter of $(1.0 \text{ to } 2.5) \times 10^4 (Jm^{-3})^{1/2}$ mixed thereinto, so that there remains the unpolymerizable organic compound in a specific amount.

How to add the unpolymerizable organic compound having a solubility parameter of $(1.0 \text{ to } 2.5) \times 10^4 (Jm^{-3})^{1/2}$, the β-hydroxypropionic acid and/or the acrylic acid dimmer, and the methoxyphenol during the distillation in the process (1) above is not especially limited. They may be added either directly in the form of powder, or in the form of solutions in the acrylic acid. Suitable devices that can be used in the process (2) above are disclosed in Japanese Examined Patent Publication No. 41637/1978 (Tokukousho 53-41637).

Conventionally, the technique of purifying acrylic acid for the production of a water-absorbent resin is known in the above patent documents. The conventional technique of purifying acrylic acid is applied to a commercially available acrylic acid having a p-methoxyphenol content of approximately 200 ppm by weight. However, such an idea has never been conceived that the unpolymerizable organic compound, the β-hydroxypropionic acid and/or the acrylic acid dimmer, and the methoxyphenol are adjusted to the unpolymerizable organic compound having a particular solubility parameter and a particular amount, the β-hydroxypropionic acid and/or the acrylic acid dimmer of a particular amount, and the methoxyphenol of a particular amount.

With the above process for obtaining acrylic acid composition, it is possible to obtain a new acrylic acid composition, i.e. acrylic acid composition having an unpolymerizable organic compound content of 1 to 1000 ppm by weight, the unpolymerizable organic compound having a solubility parameter of $(1.0 \text{ to } 2.5) \times 10^4 (Jm^{-3})^{1/2}$. Such an acrylic acid composition is preferably used for raw material used in the polymerization for the production of a water-absorbent resin.

Such acrylic acid composition contains a small amount of water (0 to 5 wt %, further 0 to 2 wt %, particularly 0 to 1 wt. %) and the aforementioned trace components (e.g. methoxyphenol). Surprisingly, as an amount of water contained in acrylic acid composition becomes large, a residual monomer content can increase. The process for producing a water-absorbent resin according to the present invention allows for production, with a high productivity, of a water-absorbent resin having an improved relationship between absorption capacity and water-soluble polymer which are conflicting properties of the water-absorbent resin, being easily controlled for polymerization reaction, being less colored, and being of high absorption properties.

(4) Basic Composition

"Basic composition" herein means a composition containing a basic compound. In the present invention, the basic composition preferably contains iron as will be described hereinafter, i.e. iron-containing compound, as well as the basic compound.

Examples of the basic compound as used in the present invention include alkaline-metal (hydrogen)carbonate, alkaline-metal hydroxides, ammonia, and organic amines. However, in order to obtain a water-absorbent resin having still higher properties, strong-alkali substances i.e. alkaline-metal hydroxides such as sodium hydroxide, potassium hydroxide, and lithium hydroxide are preferable. Among the alkaline-metal hydroxides listed above, sodium hydroxide is particularly preferred. Sodium hydroxide usually has a sodium carbonate and/or sodium chloride content of about 0 to 5%. Such a sodium hydroxide is also applied preferably to the present invention.

As described in Patent document 3, it has been known that a heavy metal content of more than 0.1 ppm by weight in an aqueous solution of a monomer increases a residual monomer content in a water-absorbent resin. On the contrary, according to the process of the present invention, i.e. the process including the step of preparing a monomer by using (i) acrylic acid containing particular trace components and (ii) a basic composition containing iron in particular amounts (0.2 to 5 ppm by weight) (based on the weight in terms of $Fe_2O_3$) (Preferably, a basic composition containing iron and caustic soda), it was found out that the process of the present invention realized shortening of a polymerization time, reduction in water-soluble component content, and a less colored water-absorbent resin.

Further, Patent document 3 discloses distillation of acrylic acid and activated carbon treatment of caustic soda, as the techniques for decreasing the heavy metal content to 0.1 ppm by weight, preferably not more than 0.02 ppm by weight. However, Patent document 3 does not disclose methoxyphenol as used in the present invention. Even if the acrylic acid of Patent document 3 has a methoxyphenol content of not less than 200 ppm by weight, methoxyphenol having a high boiling point (p-methoxyphenol has a boiling point of 113 to 115° C./5 mmHg) is removed by distillation and purification of the acrylic acid (boiling point: 139° C.) as described in Patent document 3. As a result of this, a methoxyphenol content in the distillated acrylic acid becomes substantially 0 ppm by weight (lower than the detection limit). In addition, Patent document 3 is totally silent about effectiveness of heavy metal for the polymerization in the process for producing a water-absorbent resin.

More specifically, a basic composition as used in the present invention contains a basic compound and iron. The basic composition has preferably an iron content (based on the weight in terms of $Fe_2O_3$) in the range of 0.01 to 5.0 ppm by weight, more preferably in the range of 0.03 to 4 ppm by weight, and still more preferably in the range of 0.05 to 2 ppm by weight, particularly preferably 0.1 to 1 ppm by weight, relative to solids content of the basic composition. The iron content of lower than 0.01 wt % causes not only the risk that the polymerization can possibly take place before the addition of a polymerization initiator, but also the possibility of a slow polymerization even with the polymerization initiator added. The iron as used in the present invention may be Fe ion; however, it is preferably trivalent iron in terms of effectiveness, particularly preferably $Fe_2O_3$. If the addition of iron such as $Fe_2O_3$ is necessary, the iron may be added to either a monomer, i.e. acrylic acid composition, or a basic composition.

(5) Subjecting an Acrylic Acid to Alkali Treatment

The process for producing a water-absorbent resin, according to the present invention, includes the step of preparing the monomer component by using the aforementioned acrylic acid containing trace components. In the step, the acrylic acid is preferably subjected to alkali treatment with the basic composition.

The alkali treatment, as referred to in the present invention, means a treatment in which the acrylic acid to be treated is subjected to neutralization at a temperature not lower than a certain temperature (high-temperature neutralization) or neutralization at a neutralization ratio not lower than a certain neutralization ratio (high neutralization). Such an alkali treatment greatly promotes the polymerization of acrylic acid. Specific examples thereof include: a process in which the acrylic acid composition is gradually added to a certain amount of basic composition to get a strong alkaline region; and a process in which the alkali treatment is carried out simultaneously with the neutralization by line-mixing the acrylic acid composition and a strong-alkali basic composition together.

As to the high-temperature neutralization, the temperature in the alkali treatment is higher than a temperature in normal neutralization. More specifically, the temperature in the alkali treatment is preferably in the range of 30° C. to the boiling point, more preferably in the range of 40° C. to the boiling point, still more preferably in the range of 50° C. to the boiling point, particularly preferably in the range of 60° C. to the boiling point. In the alkali treatment, in cases where the temperature is low and where no strong alkali is used and further where the neutralization has not yet been completed, the polymerizability is so low that inferior results may be also obtained with regard to the properties even if a purified acrylic acid is used.

As to the high neutralization, these alkali treatments are preferably in the presence of an excess of alkali so that the neutralization ratio of acrylic acid is substantially 100 mol %. The amount of alkali can be more than is necessary to neutralize 100 mol % of the acrylic acid.

Examples of the basic compound contained in the basic composition as used for the neutralization include alkaline-metal hydroxides such as sodium hydroxide, potassium hydroxide, and lithium hydroxide. Among the alkaline-metal hydroxides listed above, sodium hydroxide is particularly preferred. In the alkali treatment, particularly, strong-alkali treatment, the acrylic acid is treated in such a manner to form an aqueous solution or dispersion including post-neutralization acrylate concentration of which is preferably 10 to 80 wt %, more preferably 20 to 60 wt %, still more preferably 30 to 50 wt %. The time of such an alkali treatment, particularly the treatment time in the case of carrying out the alkali treatment in the presence of an excess of the alkali, is appropriately determined in the range of preferably 1 second to 2 hours, more preferably 5 seconds to 1 hour.

Furthermore, the alkali treatment is carried out in the presence of oxygen for stability. Preferably, the alkali treatment is carried out in a state where the aqueous acrylic acid (or salt) solution, i.e. an aqueous solution of acrylic acid composition, contains oxygen preferably in the range of 0.5 to 20 ppm, more preferably 1 to 15 ppm, still more preferably 1.5 to 10 ppm. In the case where the oxygen content is low, there are problems of the stability of the monomer in the alkali treatment. The alkali treatment is preferably carried out under an oxygen or air atmosphere, more preferably, while oxygen or air is blown in and/or drawn in. The oxygen content is measurable with a dissolved oxygen meter (e.g. membrane-type polarograph). The monomer thus obtained has preferably a turbidity (specified by JIS K-0101) of not more than 0.5.

(6) Another Monomer

The monomer includes acrylic acid and/or its salt in the range as previously defined. Such a monomer may be used with another monomer in combination. In other words, in the present invention, the acrylic acid composition may contain acrylic acid and/or its salt in the aforementioned range and also contain another monomer.

Examples of this monomer that can be used in combination include monomers as disclosed in U.S. patents and European patents as will be described later. Specific examples thereof further include copolymers as obtained by copolymerizing the acrylic acid and/or its salt with, for example, water-soluble or hydrophobic unsaturated monomers such as methacrylic acid, (anhydrous) maleic acid, fumaric acid, crotonic acid, itaconic acid, vinylsulfonic acid, 2-(meth)acrylamido-2-methylpropanesulfonic acid, (meth)acryloxyalkanesulfonic acid, and their alkaline metal salts and ammonium salts, and further, N-vinyl-2-pyrrolidone, N-vinylacetamide, (meth)acrylamide, N-isopropyl(meth)acrylamide, N,N-dimethyl(meth)acrylamide, 2-hydroxyethyl (meth)acrylate, methoxypolyethylene glycol (meth)acrylate, polyethylene glycol (meth)acrylate, isobutylene, and lauryl (meth)acrylate.

The crosslinking method as used in the present invention is not especially limited, but examples thereof include: (A) a method which involves the step of adding a cross-linking agent during and/or after the polymerization, thereby post-crosslinking; (B) a method which involves radical crosslinking with radical polymerization initiators; and (C) a method which involves radiation crosslinking such as by electron beams. However, a preferable one is (D) a method which involves the steps of beforehand adding a predetermined amount of an internal cross-linking agent to a monomer, and then carrying out polymerization simultaneously with and/or after which a crosslinking reaction is carried out.

Examples of the internal cross-linking agent as used in the present invention include N,N'-methylenebisacrylamide, (poly)ethylene glycol di(meth)acrylate, (poly)propylene glycol di(meth)acrylate, (polyoxyethylene) trimethylolpropane tri(meth)acrylate, trimethylolpropane di(meth)acrylate, polyethylene glycol di(β-acryloyloxypropionate), trimethylolpropane tri(β-acryloyloxypropionate), poly(meth)allyloxyalkanes, polyethylene glycol diglycidyl ether, ethylene glycol, polyethylene glycol, and glycerol. These internal-crosslinking agents may be used either alone or in combinations with each other. Incidentally, when at least one internal-crosslinking agent is used, it is favorable in consideration of, for example, the absorption properties of the resultant water-absorbent resin that a compound with at least two polymerizable unsaturated groups as an essential component is used during the polymerization.

The amount of the above internal cross-linking agent is preferably in the range of 0.005 to 2 mol %, more preferably 0.01 to 1 mol %, still more preferably 0.05 to 0.2 mol %, relative to the aforementioned monomer. In the case where the amount of the above internal cross-linking agent is smaller than 0.005 mol % or larger than 2 mol %, there is a possibility that the desired absorption properties may not be obtained.

When the monomer component is used in the form of its aqueous solution in the case where reversed-phase suspension polymerization or aqueous solution polymerization is carried out in the polymerization step, the concentration of the monomer component in this aqueous solution (hereinafter referred to as "aqueous monomer solution") is in the range of preferably 10 to 70 wt %, more preferably 15 to 65 wt %, still more preferably 30 to 55 wt %, in terms of the resulting properties, although not especially limited. In addition, when the above aqueous solution polymerization or reversed-phase suspension polymerization is carried out, a solvent other than water may be used therewith in combination if necessary, and the kind of this solvent as used in combination is not especially limited.

In carrying out the polymerization, a water-soluble resin or a water-absorbent resin of 0 to 50 wt %, for example, preferably 0 to 20 wt %, as various foaming agents (e.g. carbonate, azo compounds, bubbles), surfactants, chelating agents, and chain transfer agents in amounts of 0 to 5 wt %, for example, preferably 0 to 1 wt % can be added for improving the properties of the water-absorbent resin.

(7) (a) Step of Forming Hydrogel Crosslinked Polymer (Hereinafter Referred to as Polymerization Step (a))

In the step of polymerizing the monomer component, from the viewpoint of the performance or the ease of controlling the polymerization, aqueous solution polymerization or reversed-phase suspension polymerization is carried out in such a manner that the above monomer component is used in the form of its aqueous solution. These polymerization methods can be carried out in an air atmosphere. The polymerization methods are preferably carried out in an atmosphere of an inert gas such as nitrogen or argon (e.g. 1% oxygen or oxygen lower than 1%). In addition, the monomer component is used for polymerization preferably after oxygen dissolved therein has sufficiently been displaced with the inert gas (e.g. oxygen lower than 1 ppm). The present invention is particularly preferable for the aqueous solution polymerization which is of high productivity and gives high properties but conventionally involves difficulty in controlling the polymerization. Examples of particularly preferable aqueous solution polymerization include continuous belt polymerization and continuous or batch kneader polymerization.

The reversed-phase suspension polymerization is a polymerization method in which the aqueous monomer solution is suspended into a hydrophobic organic solvent, and examples thereof are disclosed in U.S. patents such as U.S. Pat. Nos. 4,093,776, 4,367,3234, 446,261, 4,683,274, 4,973,632, and 5,244,735. The aqueous solution polymerization is a polymerization method in which the aqueous monomer solution is polymerized without using any dispersion solvent, and examples thereof are disclosed in U.S. patents such as U.S. Pat. Nos. 4,625,001, 4,873,299, 4,286,082, 4,985,518, 5,124, 416, 5,250,640, 5,264,495, 5,145,906, and 5,380,808, and in European patents such as EP 0811636, EP 0955086, and EP 0922717. Monomers, cross-linking agents, polymerization initiators, and other additives which are described in the patent documents listed above are applicable to the present invention.

Furthermore, in the present invention, on the occasion when the aforementioned monomer component is polymerized, the total time between the end of the preparation of the monomer component and/or neutralization of the acrylic acid and the initiation of the polymerization is preferably as short as possible in order to attain (i) the improved absorption properties and (ii) the less colored water-absorbent resin, both of which are the goals of the present invention. Specifically, the polymerization is initiated preferably within 24 hours, more preferably within 12 hours, still more preferably within 3 hours, particularly preferably within 1 hour, after the preparation of the monomer component and/or neutralization of the acrylic acid. Industrially, the neutralization and/or the preparation of the monomer component are carried out in large quantities in tanks. Therefore it is usual that the residence time exceeds 24 hours. However, it has been discovered by the present inventors that the longer time it is after the preparation of the monomer component and/or neutralization of the acrylic acid, the more the residual monomer content and the coloration are deteriorated. Thus, to shorten the residence time, the neutralization and the preparation of the monomer component are continuously made to carry out the polymerization batchwise or continuously. Preferably, the polymerization is carried out continuously.

On the occasion when the above aqueous monomer solution is polymerized, at least one of the following polymerization initiators, for example, can be used: persulfate salts such as potassium persulfate, ammonium persulfate, and sodium persulfate; and t-butyl hydroperoxide, hydrogen peroxide, 2,2'-azobis(2-amidinopropane) dihydrochloride, 2-hydroxy- 1-phenylpropan-1-one, and benzoin methyl ether. Furthermore, a redox initiator is also available by using the above polymerization initiator jointly with a reducing agent which promotes decomposition of the above polymerization initiator and thus combining both with each other. Examples of the above reducing agent include: sulfurous acid (or (bi) sulfite) such as sodium sulfite and sodium hydrogensulfite; L-ascorbic acid (or its salts); reducible metals (or their salts) such as ferrous salts; and amines; and preferably used is a redox polymerization initiator combining the reducing agent with the persulfate salt and/or the peroxide, but there is no particular limitation thereto. The amount of the above polymerization initiator or reducing agent as used is usually in the range of preferably 0.001 to 2 mol %, more preferably 0.01 to 0.5 mol %, relative to the monomer component.

Of these polymerization initiators, preferably for attaining still lower colorability and lower yellowing of the water-absorbent resin of the present invention, the hydrogen peroxide and/or the (hydrogen)sulfite, more preferably the hydrogen peroxide, are used. Other polymerization initiators, particularly the persulfate or the azo compounds, may further be used in combination with the hydrogen peroxide and/or (hydrogen) sulfite. The quantity of the hydrogen peroxide and/or the (hydrogen)sulfite as used is preferably in the range of 0.00001 to 0.1 g/(mol of monomers), more preferably 0.0001 to 0.01 g/(mol of monomers), and further is smaller than that of the above other polymerization initiators as used jointly therewith. Incidentally, the azo compounds display a good effect on a low coloring, but excessive use of the persulfate brings about property deterioration and/or coloration. Therefore the persulfate are used in combination preferably in the aforementioned range.

In addition, the polymerization reaction may be carried out either by irradiating the reaction system with active energy rays, such as radiations, electron beams, and ultraviolet rays, instead of using the above polymerization initiator, or by a combined use of these active energy rays with the above polymerization initiator.

The reaction temperature and time in the above polymerization reaction is not particularly limited and may appropriately be set according to factors such as the respective kinds of the hydrophilic monomer and polymerization initiator and the reaction temperature. However, the polymerization is usually carried out at not higher than the boiling point preferably within 3 hours, more preferably within 1 hour, still more preferably within 0.5 hour, and at a peak temperature of preferably not higher than 150° C., more preferably in the range of 90 to 120° C. In addition, it is also preferable that water and/or acrylic acid as vaporized during the polymerization is, if necessary, collected and then recycled to the process for producing the water-absorbent resin.

In addition, the present invention is fit for production, particularly, continuous production, on a large scale of not smaller than a certain quantity per line. There is a possibility that the effects of the present invention may not sufficiently be displayed in production on a laboratory level or in production at pilot or small-scale plants. However, as to production on a large scale, particularly, of preferably not smaller than 300 Kg/hour, more preferably not smaller than 500 Kg/hour, still more preferably not smaller than 700 Kg/hour, in terms of production per line, it has been discovered by the present inventors that, also from the viewpoint of such as monomer stability and polymerization rate, unless the present invention is applied thereto, the desired water-absorbent resin having sufficient properties is not obtained.

(8) (b) Step of Drying Hydrogel Crosslinked Polymer by Application of Heat (Hereinafter Referred to as Drying Step (b))

If necessary, the hydrogel crosslinked polymer having been obtained in the polymerization step (a) is disintegrated into small pieces with a gel pulverizer or the like as needed. The disintegrated resultant is dried under a particular temperature condition. Thereafter, if necessary, the dried resultant is pulverized or classified, and further granulated and crosslinked under a particular temperature condition. The water-absorbent resin according to the present invention has high properties. Undergoing the foregoing steps realizes the water-absorbent resin having further improved properties and a reduced odor.

In addition, in order to attain the objects of the present invention, i.e. the reduction of a residual monomer content and a less colored water-absorbent resin, the time from the end of the polymerization, through a gel-pulverizing step if necessary, until the start of the drying is preferably as short as possible. Specifically, the hydrogel crosslinked polymer starts to be dried (is placed into a dryer) preferably within 1 hour, more preferably within 0.5 hour, still more preferably within 0.1 hour, after the polymerization is completed. In addition, in order to attain the reduction of a residual monomer content and a less colored water-absorbent resin, the temperature of the hydrogel crosslinked polymer is controlled to be preferably in the range of 50 to 80° C., more preferably 60 to 70° C., for the duration between the end of the polymerization and the start of the drying. On industrial occasions, the polymerization is carried out in large quantities, therefore it is also usual that the residence time, after the polymerization, exceeds 3 hours. However, it has been discovered by the present inventors that as the time increases before the start of the drying and/or as the temperature deviates from the above range, the residual monomer content increases or a resultant water-absorbent resin becomes remarkably colored. Thus, preferably, continuous polymerization and continuous drying are carried out to shorten the residence time.

In the present invention, the drying is primarily the operation for removing water, and also for removing an unpolymerizable organic compound having the solubility parameter defined previously.

The solid content of the resin as determined from its weight loss caused by drying (by heating 1 g of powder or particles at 180° C. for 3 hours) is adjusted to be preferably not less than 80 wt %, more preferably in the range of 85 to 99 wt %, still more preferably 90 to 98 wt %, particularly preferably 92 to 97 wt %. In addition, a drying temperature is not particularly limited, but is preferably such that heating in the step (b) is carried out at a temperature not lower than the boiling temperature of the unpolymerizable organic compound. Specifically, the drying temperature is preferably in the range of 100 to 300° C., more preferably 150 to 250° C. (defined based on a temperature of heating medium).

Examples of usable drying methods include various methods such as: heat-drying; hot-air drying; vacuum drying; infrared drying; microwave drying; drum drier drying; dehydration by azeotropy with hydrophobic organic solvents; and high-moisture drying by high-temperature steaming. The preferred drying method is the hot-air drying with a gas having a dew point of preferably 40 to 100° C., more preferably 50 to 100° C., still more preferably 60 to 90° C., in terms of properties of the water-absorbent resin and efficiency in removal of the unpolymerizable organic compound.

(9) Surface-Crosslinking Step (c)

Next, a further explanation is made about the surface-crosslinking in the present invention. The "surface-crosslinking" of the water-absorbent resin means further forming a portion having high crosslinking density in surface layers (neighborhoods of surfaces: neighborhoods usually within several tens of μm from the surfaces) of the water-absorbent resin having a uniformly crosslinked structure inside the polymer. The water-absorbent resin obtained in the present invention has a low water-soluble component content and a high absorption capacity, thus attaining excellent surface-crosslinking effects thereon, exerting more excellent properties and performances, increasing its absorption capacity under pressure (AAP) and liquid permeability under pressure (PPUP), and reducing its odor.

Various surface-crosslinking agents are usable for carrying out the foregoing surface-crosslinking. However, in terms of the properties, crosslinking agents that can react with a carboxyl group are generally used. Examples of such crosslinking agents are: polyhydric alcohol compounds; epoxy compounds; polyamine compounds or condensation products of polyamine compounds and haloepoxy compounds; oxazoline compounds; mono-, di-, or polyoxazolidinone compounds; polyvalent metal salts; and alkylene carbonate compounds.

The surface-crosslinking agent as used in the present invention is specifically exemplified in such as U.S. Pat. Nos. 6,228,930, 6,071,976, and 6,254,990. Examples thereof include: polyhydric alcohol compounds such as mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyamine compounds such as ethylenediamine, diethylenetriamine, triethylenetetramine, tetraethylenepentamine, pentaethylenehexamine, polyethylenimine, and polyamidopolyamines; haloepoxy compounds such as epichlorohydrin, epibromohydrin and α-methylepichlorohydrin; condensation products between the above polyamine compounds and the above haloepoxy compounds; oxazolidinone compounds such as 2-oxazolidinone; and alkylene carbonate compounds such as ethylene carbonate. However, there is no particular limitation. Of these crosslinking agents, at least the polyhydric alcohols are used preferably for maximizing the effects of the present invention, and polyhydric alcohols having 2 to 10 carbon atoms, preferably 3 to 8 carbon atoms, are used.

The quantity of the surface-crosslinking agent as used depends upon factors such as the types of the compounds used and combinations thereof, but is preferably in the range of 0.001 to 10 parts by weight, more preferably 0.01 to 5 parts by weight, relative to 100 parts by weight of the solid content of the resin. In the present invention, water is preferably used for the surface-crosslinking. The quantity of water, as used on this occasion, depends upon the water content of the water-absorbent resin as used, but is usually in the range of preferably 0.5 to 20 parts by weight, more preferably 0.5 to 10 parts by weight, relative to 100 parts by weight of the water-absorbent resin. In addition, in the present invention, a hydrophilic organic solvent may be used as an alternative to water. The quantity of the hydrophilic organic solvent, as used on this occasion, is usually in the range of preferably 0 to 10 parts by weight, more preferably 0 to 5 parts by weight, still more preferably 0 to 3 parts by weight, relative to 100 parts by weight of the water-absorbent resin. The temperature of the crosslinking agent solution is preferably set in the range of 0° C. to boiling point, more preferably 5 to 50° C., still more preferably 10 to 30° C., in terms of the mixability and stability. In addition, before mixing with crosslinking agent solution, the temperature of the water-absorbent resin powder is preferably in the range of 0 to 80° C., more preferably 40 to 70° C., in terms of the mixability.

Furthermore, in the present invention, one preferred mixing method is a method including the steps of premixing the surface-crosslinking agent with water and/or the hydrophilic organic solvent, if necessary, and then spraying or dropwise adding (preferably, spraying) the resultant aqueous solution to the water-absorbent resin to mix them together. The size of the liquid droplets as sprayed averages preferably 1 to 300 μm, more preferably 10 to 200 μm. In addition, in the mixing step, there may be allowed to coexist water-insoluble fine-particulate powder and/or surfactants within the range not damaging the effects of the present invention, for example, within the range of 0 to 10 wt %, preferably 0 to 5 wt %, more preferably 0 to 1 wt %, relative to the water-absorbent resin. The surfactants as used and their quantities are exemplified in the International publication WO2005JP1689 (International filing date: Feb. 4, 2005).

A preferable mixing apparatus as used for the aforementioned mixing step needs to be able to generate great mixing power to ensure homogeneous mixing. Various mixing machines are usable in the present invention, but preferably they are high-speed agitation type mixers, particularly preferably, high-speed agitation type continuous mixers. Examples of such mixers are Turbulizer (product name; produced by Hosokawa Milkron Co., Ltd. of Japan) and Lödige Mixer (product name; produced by Gebruder Lödige Maschinenbau GmbH of Germany).

After mixing with the surface-crosslinking agent, the resulting water-absorbent resin preferably is subjected to the heating treatment. The above heating treatment is preferably carried out under the conditions where the heating temperature in the step (c) is not lower than a boiling point of the unpolymerizable organic compound (defined based on a temperature of heating medium). The heating temperature is preferably in the range of 120 to 250° C., more preferably 150 to 250° C. The heating time is preferably in the range of 1 minute to 2 hours. The heating treatment can be carried out by using conventional dryers or heating-furnaces. Examples of the dryers include channel type blending dryers, rotary dryers, disk dryers, fluidized-bed dryers, gas blowing type (pneumatic type) dryers, and infrared dryers. In addition, after being heated, the water-absorbent resin may be cooled, if necessary.

These surface-crosslinking methods are also disclosed in: various European patents such as European Patent Nos. 0349240, 0605150, 0450923, 0812873, 0450924, and 0668080; various Japanese patents such as Japanese Unexamined Patent Publication Nos. 242709/1995 and 224304/1995; various U.S. patents such as U.S. Pat. Nos. 5,409,771, 5,597,873, 5,385,983, 5,610,220, 5,633,316, 5,674,633, and 5,462,972; and various international patent publications such as WO 99/42494, WO 99/43720, and WO 99/42496. These surface-crosslinking methods are also applicable to the present invention.

(10) Properties and Shape of the Water-Absorbent Resin

The shape of the water-absorbent resin as obtained in the present invention is not especially limited, but examples thereof include: particulate or powder form such as irregular pulverized form and spherical form; and gel form, sheet form, rodlike form, fibrous form, and film form. In addition, the resin may be combined with or supported on materials such as fibrous materials. However, generally, the water-absorbent resin is preferably in particulate or powder form, considering the uses for the water-absorbent resin, such as absorbent articles and gardening and tree planting. In the case where the water-absorbent resin is in powder form, it may be granulated particles or primary particles, and the weight-average particle diameter thereof before or after the surface-crosslinking is usually in the range of 10 to 2000 μm. In the present invention, the granulated particles are also referred to as agglomerate particles. In terms of the properties, the weight-average particle diameter is preferably in the range of 100 to 1000 μm, more preferably 200 to 600 μm, particularly preferably 300 to 500 μm. The quantity of particles having particle diameters in the range of 850 to 150 μm is in the range of 90 to 100 wt %, in the range of 95 to 100 wt %, particularly in the range of 98 to 100 wt %.

The water-absorbent resin produced by the production process of the present invention and the water-absorbent resin of the present invention improve the relationship between absorption capacity and water-soluble polymer, which are conflicting properties of a water-absorbent resin. Thus, the water-absorbent resin of the present invention can have still higher properties by being subjected to surface-crosslinking.

More specifically, the water-absorbent resin produced by the production process of the present invention and the water-absorbent resin according to the present invention preferably has an absorption capacity of not less than 15 g/g, more preferably not less than 20 g/g, still more preferably not less than 23 g/g, yet more preferably 25 g/g for a physiological saline solution under pressure (4.8 kPa). In addition, the absorption capacity for a physiological saline solution under pressure (1.9 kPa) is also usually not less than 15 g/g, preferably not less than 20 g/g, more preferably not less than 25 g/g, still more preferably 28 g/g, particularly preferably not less than 32 g/g. The absorption capacity without pressure (GVs) is also not less than 25 g/g, more preferably not less than 28 g/g, particularly preferably not less than 32 g/g. There are no particular upper limits for the absorption capacity under pressure and the absorption capacity without pressure. However, the upper limits therefor are usually in the order of 60 g/g, in terms of (i) balance with other properties and (ii) costs.

Furthermore, liquid-permeability under pressure (PPUP) is preferably in the range of 20 to 100%, more preferably 30 to 100%, still more preferably 40 to 100%, most preferably 50 to 100%.

Note that, the liquid permeability under pressure, which is different from the absorption capacity under pressure (AAP: 0.9 g), is a measure of the stability of the absorption capacity under pressure (AAP) (freedom from reduction in absorption capacity under pressure) when the amount of water-absorbent resin (the amount of resin per unit area in measurement) is increased from 0.90 g to 5.0 g. The liquid permeability under pressure is a new parameter defined in the present invention. For example, the amount of water-absorbent resin (the amount of resin per unit area in measurement) can vary by site even in the same diaper. Varied absorption capacity under pressure (AAP), which is caused by the amount of water-absorbent resin varying by site in the diaper, is the cause of degraded properties of the diaper in actual use. When the liquid permeability under pressure (PPUP) defined in Example as will be hereinafter described is very high, the diaper can stably exhibit high properties, regardless of the amount (concentration) of water-absorbent resin in the diaper, and can also exhibit a high liquid permeability. Details of the liquid permeability under pressure (PPUP) is described in Japanese Patent Application No. 109779/2005 (filed on Apr. 6, 2005) and the descriptions of Japanese Patent Application No. 109779/2005 are also applied to the present invention.

The water-soluble component content of the water-absorbent resin obtained in the production process of the present invention is preferably not more than 25 wt %, more preferably not more than 15 wt %, still more preferably 10 wt %. Further, a GEX value (defined in Example) defined according to the relationship between absorption capacity (GVs) and a soluble content is preferably not less than 17, more preferably not less than 18, particularly preferably not less than 19.

In addition, as is specified in the below-mentioned description of examples of some preferred embodiments of the present invention and in the aforementioned object of the present invention, the water-absorbent resin produced by the production process of the present invention and the water-absorbent resin of the present invention are less colored (little or no yellowing coloration), and have a low residual monomer content. Specifically, its colored state indicates a YI value (Yellow Index, see European Patent Nos. 0942014 and 1108745) preferably in the range of 0 to 15, more preferably 0 to 13, still more preferably 0 to 10, most preferably 0 to 5, so there is almost no tinge of yellow. Furthermore, the residual monomer content is low and preferably in the range of 0 to 400 ppm by weight, more preferably 0 to 300 ppm by weight.

In order to cause the water-absorbent resin produced by the production process of the present invention and the water-absorbent resin of the present invention to have various functions, materials such as chelating agents, oxidizers, reducing agents such as (hydrogen)sulfite, chelating agents such as amino carboxylic acid, water-insoluble inorganic powder or water-insoluble organic powder, deodorizers, antimicrobial agents, and polymer polyamine, in a quantity of 0 to 10 parts by weight, preferably 0 to 1 parts by weight.

The water-absorbent resin produced by undergoing the drying step (b) and the surface-crosslinking step (c) is finally controlled such that a content of a unpolymerizable organic compound having the above-specified solubility parameter is not more than 10 ppm by weight. In terms of cost effectiveness and absorption properties of the water-absorbent resin, the water-absorbent resin has a unpolymerizable organic compound content of preferably not less than 0.01 ppm by weight, more preferably not less than 0.01 ppm by weight and not more than 5 ppm by weight, particularly preferably not less than 0.01 ppm by weight and not more than 1 ppm by weight. If the water-absorbent resin has the unpolymerizable organic compound content of more than 10 ppm by weight, it raises the problem that products from such a water-absorbent resin have unpleasant odor. On the other hand, the water-absorbent resin in which the unpolymerizable organic compound content is adjusted to less than 0.01 wt % is not preferred because such a water-absorbent resin might exhibit low absorption properties by passing excess heat treatments in the drying step and the surface-crosslinking step.

Further, the water-absorbent resin includes has an iron content of not less than 0.01 ppm by weight and not more than 1 ppm by weight, preferably not less than 0.01 ppm by weight and not more than 0.5 ppm by weight. Because of this, when such a water-absorbent resin is applied to absorbent articles, e.g. disposable diapers, the absorbent articles offer an excellent balance of stable absorption-properties in its use and easy-degradation after the disposal of used absorbent articles.

The water-absorbent resin having an iron content of less than 0.01 ppm by weight is not preferred because the absorbent articles produced from such a water-absorbent resin become hard to be degraded after their use. Further, the water-absorbent resin having an iron content of more than 1 ppm by weight is not preferred because such a water-absorbent resin causes the degradation of the absorbent articles, e.g. disposable diapers, in use.

(11) Uses of the Water-Absorbent Resin According to the Present Invention

The process according to the present invention provides the easy production of a water-absorbent resin having good absorption properties in excellent balance between the absorption capacity without pressure (=GVs=Gel Volume in saline=Centrifuge retention capacity), the absorption capacity under pressure (AAP), and the soluble content. The resulting water-absorbent resin is widely used for various purposes such as agricultural and horticultural water-retaining agents, industrial water-retaining agents, humidity-absorbing agents, dehumidifying agents, and building materials, but the water-absorbent resin according to the present invention is particularly preferably used for sanitary materials such as disposable diapers, incontinent pads, mother's breast pads (nursing pads), and sanitary napkins.

Furthermore, the water-absorbent resin according to the present invention is so excellent with regard to the above properties being in good balance that the water-absorbent resin can be used in the sanitary materials (e.g. disposable diapers) in high concentrations where the water-absorbent resin concentration (weight ratio of the water-absorbent resin to the total weight of the water-absorbent resin and fibrous materials), is preferably 30 to 100 wt %, more preferably 40 to 100 wt %, still more preferably 50 to 95 wt %.

EXAMPLES

Hereinafter, the present invention will be described according to Examples below. However, the present invention is not limited to the descriptions of Example. In addition, the properties, as recited in the claims of the present invention and in Examples of the present invention, were determined by the following measurement methods.

(1) Absorption capacity without pressure (=GVs=Gel Volume in saline=Centrifuge retention capacity)

0.2 g of water-absorbent resin was uniformly placed into a bag (60 mm×60 mm) made of nonwoven fabric. The bag was sealed and then immersed into 100 g of a 0.9 wt % aqueous sodium chloride solution (physiological saline solution) of which the temperature had been adjusted to 25 (±3) ° C. After 60 minutes, the bag was pulled up and then drained of water by a centrifugal force of 250 G with a centrifugal separator for 3 minutes, and then the weight W1 of the bag was measured. In addition, the same procedure as the above was carried out without the water-absorbent resin, and the resultant weight W2 was measured. Then, the absorption capacity was calculated from these W1 and W2 according to the following equation (1):

$$GVs=(W1-W2)/0.2-1 \quad \text{(Equation 1)}.$$

(2) Water-Soluble Polymer Content (which May be Also Referred to as "Soluble Component Content")

Into a plastic receptacle of 250 ml in capacity having a lid, 184.3 g of 0.90 wt % aqueous sodium chloride solution was weighed out. Then, 1.00 g of water-absorbent resin was added to this aqueous solution, and they were stirred for 16 hours, thereby soluble components were extracted from the resin. The resultant extract liquid was filtrated with a filter paper (produced by ADVANTEC Toyo Co., Ltd., trade name: (JIS P 3801, No. 2), thickness: 0.26 mm, diameter of captured particles: 5 μm), and then 50.0 g of the resultant filtrate was weighed out and used as a measuring solution.

To begin with, only the physiological saline solution was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml). The same titration procedure was carried out also for the measuring solution, thus obtaining titration amounts ([NaOH] ml and [HCl] ml). For example, if the water-absorbent resin comprised acrylic acid and its sodium salt in known amounts, the soluble component content (content of an extracted water-soluble polymer as a main component) of the water-absorbent resin was calculated from the average molecular weight of the monomers and the titration amounts, as obtained from the above procedures, in accordance with the following equation (2). In the case of unknown amounts, the average molecular weight of the monomers was calculated from the neutralization ratio as determined by the titration.

$$\text{Soluble component content(wt \%)}=0.1\times(\text{average molecular weight})\times 184.3\times 100\times([HCl]-[bHCl])/1000/1.0/50.0 \quad \text{(Equation 2)}.$$

$$\text{Neutralization ratio(mol \%)}=[1-([NaOH]-[bNaOH])/([HCl]-[bHCl])]\times 100 \quad \text{(Equation 3)}.$$

(3) GEX Value

Normally, the higher the absorption capacity (GVs), the higher the water-soluble component content. Thus, important for a water-absorbent resin is the relationship between a GVs value and a water-soluble component content (x), which are conflicting properties of the water-absorbent resin. The GEX value is a measure for evaluating the above relationship in the case when x exceeds 1 weight %. The higher the GEX value, the higher the performance.

When the GVs value and the soluble component content are denoted by y (g/g) and x (weight %), respectively, the GEX value is defined by the following equation 4:

$$GEX\text{ value}=(\gamma)/\ln(x) \quad \text{(equation 4)}.$$

Note that, as to the GVs value γ (g/g) and the soluble component content (wt %) required for the calculation of the GEX value, the values obtained in Sections (1) and (2) above are used.

(4) Residual Monomer Content

The residual monomer (acrylic acid and its salt) content of the water-absorbent resin powder, after drying, was determined in the following way. In Section (2) above, a filtrate, as separately prepared after stirring for two hours, was UV-analyzed by liquid chromatography to also analyze the residual monomer content ppm (relative to water-absorbent resin) of the water-absorbent resin. In addition, the residual monomer content of the hydrogel crosslinked polymer, before drying, was determined by: stirring a finely disintegrated hydrogel crosslinked polymer of about 500 mg in solid resin content for 16 hours; and then UV-analyzing its filtrate by liquid chromatography likewise; and then correcting the solid content.

(5) Absorption Capacity Under Pressure (AAP)

Absorption capacity for 0.9 wt % aqueous sodium chloride solution under pressure of 4.8 kPa (AAP: 0.90 g/Absorbency Against Pressure)

A stainless metal gauze, which was a screen of 400 meshes (mesh opening size: 38 μm), was fused to a bottom of a plastic supporting cylinder having an inner diameter of 60 mm. Then, onto the above metal gauze, there was uniformly spread 0.900 g of water-absorbent resin (particulate water-absorbing agent), and further thereon, there were mounted a piston (cover plate), wherein the piston had an outer diameter of only a little smaller than 60 mm and made no gap with the inner wall surface of the supporting cylinder, but was not hindered from moving up and down. Then, the weight W3 (g), i.e. total weight of the supporting cylinder, the water-absorbent resin (or particulate water-absorbing agent), and the piston was measured. Onto this piston, a load was placed on the piston, wherein the load was adjusted so that a load of 4.9 kPa including the weight of the piston could uniformly be applied to the water-absorbent resin (or particulate water-absorbing agent). This completed one set of measurement apparatus. A glass filter having a diameter of 90 mm and a thickness of 5 mm was mounted inside a Petri dish having a diameter of 150 mm, and then a physiological saline solution of which the temperature was adjusted to 25±2° C. was added up to the same level as the upside of the glass filter, on which a filter paper (produced by Toyo Roshi Kaisha, Ltd.; No. 2) having a diameter of 9 cm was then mounted so that its entire surface would be wetted, and further, an excess of liquid was removed.

The one set of measurement apparatus was mounted on the above wet filter paper, thereby getting the liquid absorbed under the load. The liquid level was topped off by adding the liquid from the upper side of the glass filter, so that the liquid was kept at a constant liquid level. After 1 hour, the one set of measurement apparatus was lifted to remove the load, and weight W4 (g) (total weight of the supporting cylinder, a swelling water-absorbent resin (or particulate water-absorbing agent), and the piston) was measured. Then, the absorption capacity under pressure (g/g) was calculated from the W3 and W4 in accordance with the following equation:

Absorption Capacity under Pressure(AAP: 0.90 g)(g/g)=(Weight $W4$(g)–Weight $W3$(g))/weight(g) of water-absorbent resin (or particulate water-absorbing agent).

The load of 4.9 kPa (0.90 g of water-absorbent resin) is also referred to as AAP 4.9 kPa. If the load is changed to 1.9 kPa, the load 1.9 kPa is referred to as AAP1.9 kPa.

(6) Liquid Permeability Under Pressure (PPUP/Permeability Potential Under Pressure)

In the measurement of the (5) absorption capacity under pressure (AAP: 0.09 g) under 4.9 kPa, the same procedure as above was carried out except that the amount of water-absorbent resin is changed from 0.900 g to 5.000 g, in order to obtain a value of the absorption capacity under pressure (AAP: 5.0 g). In this procedure, a high absorption capacity under pressure (AAP: 5.0 g) can possibly cause an extremely high layer of a swollen water-absorbent resin (or particulate water-absorbing agent). In view of this, the supporting cylinder as used needs to be of a sufficient height. By using the absorption capacities under pressure (AAP: 0.90 g and AAP: 5.0 g) as obtained in the above procedure, a liquid permeability under pressure (PPUP) is obtained by the following equation:

Liquid permeability under pressure(PPUP)(%)=(AAP: 5.0 g(g/g)/AAP:0.90 g(g/g))×100.

(7) Peak Time and Induction Time:

The temperature of the monomer or of the resultant polymer gel during the polymerization was measured with a thermometer. Assume that the time (minutes) between the addition of an initiator and the rise in temperature of the monomer or of the resultant polymer gel is defined as an induction time, and the time between the addition of an initiator and the reach to the maximum temperature (peak temperature) of the polymerization system is defined as a peak time.

(8) Weight-Average Particle Diameter (D50):

The water-absorbent resin powder or water-absorbing agent was classified by sieving with JIS standard sieves (JIS Z8801-1(2000) or the like sieves) having mesh opening sizes of such as 850 µm, 710 µm, 600 µm, 500 µm, 425 µm, 300 µm, 212 µm, 150 µm, 106 µm, and 75 µm, and then the percentages of the residues on these sieves were plotted on a logarithmic probability paper. Therefrom, the weight-average particle diameter (D50) was read. The classification was carried out as follows. Under conditions of a room temperature (20 to 25° C.) and a relative humidity of 50±5% RH, 10 g of water-absorbent resin powder or water-absorbing agent was placed onto the JIS standard sieves (THE IIDA TESTING SIEVE: internal diameter=80 mm), and then classified with a sieve shaker (sieve shaker produced by IIDA SEISAKUSHO; Type: ES-65) for 10 minutes. The weight-average particle diameter (D50) is, as described in U.S. Pat. No. 5,051,259 and other publications, a size of a particular mesh opening of a standard sieve capable of causing 50 wt % particles relative to the entire particles to pass through it.

(9) Coloration Evaluation of Water-Absorbent Resin (YI Value)

This was carried out in accordance with European Patent Nos. 942014 and 1108745. Specifically, the coloration evaluation of the water-absorbent resin powder was carried out in the following way using a spectroscopic color difference meter (SZ-Σ80 COLOR MEASURING SYSTEM, produced by Nippon Denshoku Kogyo Co., Ltd.). About 6 g of the water-absorbent resin was filled into the below-mentioned powder-paste sample stand (filling of about 60% of this sample stand) to measure the surface color (YI value (Yellow Index)) of the water-absorbent resin using the above spectroscopic color difference meter under its set conditions (reflection measurement/appendix powder-paste sample stand (inner diameter: 30 mm)/standard round white board No. 2/30 mm Φ projector pipe for powder-paste as the standard) under conditions of a room temperature (20 to 25° C.) and a relative humidity of 50 RH %.

In addition, color difference (L, a, b) or WB (Hunter Color) which is another yardstick is also measurable at the same time by the same method with the same apparatus as the above. The larger L/WB and the smaller a/b indicate that dye coloring is lower and that the color is nearer to being substantially white.

(10) Odor Evaluation

A sample was prepared by the following manner: 2 g of water-absorbent resin particles are sprayed in a polypropylene cup having an internal diameter of 55 mm and a height of 70 mm, and 50 g of ion-exchanged water was poured into the cup so that the water-absorbent resin particles were gelled. After the gelation, the gelled water-absorbent resin particles were sealed hermetically and heated at 30° C. for 1 hour. Thereafter, the odor of the gelled water-absorbent resin particles was evaluated by 10 adult test subjects. As to a polymer gel, the odor of the polymer gel was evaluated with the polymer gel itself directly placed into the polypropylene cup, without being mixed with ion-exchanged water.

The evaluation was determined in the following manner: Evaluation values, which indicate the degree of odor, were given in five levels from "no odor" (0 point) to "strong odor" (5 point). From the evaluation values reported by the 10 adult test subjects, the average evaluation value was determined to obtain an odor point. The odor point low in number indicates less odors.

Production Example 1

Commercially available acrylic acid (special-grade reagent available from Wako Pure Chemical Industries, Ltd.;

p-methoxyphenol content=200 ppm by weight), as obtained by catalytic gas phase oxidation, was supplied into the column bottom of a high-boiling-point-impurities-separating column having fifty dual-flow perforated plates, and then distilled in a reflux ratio of 1 and then further re-distilled, thus obtaining an acrylic acid composition (1) (also referred to as purified acrylic acid) comprising acrylic acid at a concentration of not less than 99% and trace amounts of impurities (mainly, water).

In the acrylic acid composition (1), a p-methoxyphenol content was ND (less than 1 ppm by weight). Also, a protoanemonin content, a furfural content, a β-hydroxypropionic acid content, and an acrylic acid dimmer content were each ND (less than 1 ppm by weight). In the acrylic acid composition (1), a phenothiazine content was 0 ppm by weight, an aldehyde content was not more than 1 ppm by weight, a maleic acid content was not more than 1 ppm by weight, an acetic acid was 200 ppm by weight, and propionic acid content was 200 ppm by weight.

Production Examples 2 through 5

Acrylic acid compositions (2) through (5) having their respective predetermined toluene contents were obtained by adding toluene, in quantities of 10 ppm by weight, 100 ppm by weight, 1000 ppm by weight, and 10000 ppm by weight, respectively (relative to solid content of acrylic acid), to the acrylic acid composition (1) as obtained in Production Example 1.

Production Examples 6 through 8

Acrylic acid compositions (6) through (8) having their respective predetermined diphenyl ether contents were obtained by adding diphenyl ether, in quantities of 10 ppm by weight, 1000 ppm by weight, and 10000 ppm by weight, respectively (relative to solid content of acrylic acid), to the acrylic acid composition (1) as obtained in Production Example 1.

Production Example 9

A 5 liter-five-necked flask of 5 liters in capacity, as equipped with two dropping funnels, a pH meter, a thermometer, and stirring blades, was charged with 1598 g of ion-exchanged water. In addition, separately, 1280 g of the acrylic acid composition (1) (consisting substantially of acrylic acid) at room temperature and 1488 g of 48 wt % aqueous sodium hydroxide solution (Fe content is 0.5 ppm by weight in terms of $Fe_2O_3$) at room temperature were placed into the two dropping funnels respectively, and the 5-litter flask was immersed into a water-cooling bath. Next, while the temperature of the neutralization reaction system in the 5-liter flask was maintained at a temperature of not higher than 35° C. under stirred conditions, the 48 wt % aqueous sodium hydroxide solution and the acrylic acid composition (1) were dropwise added into the flask at the same time as each other. The dropwise addition of the acrylic acid composition (1) was completed in about 35 minutes, and the dropwise addition of the 48 wt % aqueous sodium hydroxide solution was completed in about 45 minutes. After the completion of the dropwise addition of the acrylic acid composition (1), its dropping funnel was washed with 100 g of ion-exchanged water, and all the used washing water was then added into the flask. Furthermore, after the completion of the dropwise addition of the 48 wt % aqueous sodium hydroxide solution, its dropping funnel was similarly washed with 100 g of ion-exchanged water, and all the used washing water was then added into the flask.

After the completion of all the dropwise additions, the temperature of the resultant solution was adjusted into the range of 20 to 35° C. to age the reaction mixture for 20 minutes. After this aging, an extremely small quantity of the acrylic acid composition (1) was dropwise added to adjust the pH to 10 (±0.1), thus obtaining an aqueous sodium acrylate solution (1) having a concentration of 37 wt % and a neutralization ratio of 100 mol %.

Production Examples 10 through 16

Aqueous sodium acrylate solutions (2) through (8) were obtained as in the production of the aqueous sodium acrylate solution (1), except that the acrylic acid composition (1) as used for the neutralization was replaced with the acrylic acid compositions (2) through (8).

Production Example 17

An acrylic acid composition (9) was obtained by adding diphenyl of 100 ppm by weight to the acrylic acid composition (1) as obtained in the Production Example 1.

Production Example 18

An acrylic acid composition (10) was obtained by adding ethyl alcohol of 1000 ppm by weight to the acrylic acid composition (1) as obtained in the Production Example 1.

Production Example 19

Aqueous sodium acrylate solutions (9) and (10) were obtained as in the production of the aqueous sodium acrylate solution (1), but the acrylic acid composition (1) as used for the neutralization was replaced with the acrylic acid compositions (9) and (10).

Production Example 20

An aqueous sodium acrylate solution (11) was obtained as in Production Example 9, but 48% of sodium hydroxide (having a Fe content of 1000 ppm by weight) was used.

Example 1

A jacketed stainless-steel twin-arm kneader of 10 liters in capacity with its internal surface coated with Teflon® was prepared as a polymerization container. This kneader is equipped with two sigma type blades of 120 mm in rotational diameter and a lid for sealing up the inside of the system. An aqueous monomer solution (1) having a monomer concentration of 37 wt % and a neutralization ratio of 75 mol % was obtained by mixing together 376.3 g of the acrylic acid composition (2) as obtained in Production Example 2, 3983 g of the aqueous sodium acrylate solution (2), i.e. a neutralized product of the acrylic acid composition (2), and 640.7 g of ion-exchanged water, and 0.10 mol % of polyethylene glycol diacrylate (molar-number-average degree "n" of addition polymerization of ethylene oxide=8.2) as an internal-crosslinking agent of 0.10 mol % (to the entire monomers).

Furthermore, while being kept at 22° C., this aqueous monomer solution (2) was charged into the sigma type twin-arm kneader, and then nitrogen gas was introduced into the solution to deaerate the solution with nitrogen gas to reduce its dissolved oxygen content to not more than 1 ppm. Next, while warm water was passed through the jacket and while the aqueous monomer solution (1) was stirred, a polymerization initiator, comprising a combination of an aqueous solution of sodium persulfate (in an amount of 0.09 g/mol) with an aqueous solution of L-ascorbic acid (in an amount of 0.005 g/mol), was added to the aqueous monomer solution (1) to initiate polymerization. After a certain time, the polymerization started and then was allowed to proceed while the resultant polymer gel was disintegrated into fine pieces, and then, after having reached the peak temperature, the polymerization was continued for another 20 minutes, thus obtaining a finely-disintegrated hydrogel crosslinked polymer (1) having diameters in the range of about 1 to about 2 mm.

The resultant hydrogel polymer (1) was spread onto a metal gauze of 850 μm and then hot-wind-dried at 180° C. (dew point: 70° C.) for 90 minutes. Next, the resultant dried product was pulverized with a vibration mill, and further then classified with a JIS standard sieve of 850 μm, thus obtaining a water-absorbent resin powder (1).

Examples 2 through 5

A water-absorbent resin powder (2) was obtained as in Example 1, but the acrylic acid composition (3) and the aqueous sodium acrylate solution (3) were used instead of the acrylic acid composition (2) and the aqueous sodium acrylate solution (2), respectively. Similarly, a water-absorbent resin powder (3) was obtained as in Example 1, but the acrylic acid composition (4) and the aqueous sodium acrylate solution (4) were used instead of the acrylic acid composition (2) and the aqueous sodium acrylate solution (2), respectively. A water-absorbent resin powder (4) was obtained as in Example 1, but the acrylic acid composition (6) and the aqueous sodium acrylate solution (6) were used instead of the acrylic acid composition (2) and the aqueous sodium acrylate solution (2), respectively. A water-absorbent resin powder (5) was obtained as in Example 1, but the acrylic acid composition (7) and the aqueous sodium acrylate solution (7) were used instead of the acrylic acid composition (2) and the aqueous sodium acrylate solution (2), respectively.

Comparative Examples 1 through 3

A comparative water-absorbent resin powder (1) was obtained as in Example 1, but the acrylic acid composition (1) and the aqueous sodium acrylate solution (1) were used. A comparative water-absorbent resin powder (2) was obtained as in Example 1, but the acrylic acid composition (5) and the aqueous sodium acrylate solution (5) were used. A comparative water-absorbent resin powder (3) was obtained as in Example 1, but the acrylic acid composition (8) and the aqueous sodium acrylate solution (8) were used.

Example 6

100 parts by weight of the water-absorbent resin powder (1) was spraywise mixed with a surface-crosslinking agent comprising 0.4 parts by weight of 1,4-butanediol, 0.6 parts by weight of propylene glycol, 3.0 parts by weight of ion-exchanged water, and 0.5 parts by weight of isopropanol, and the resultant mixture was heat-treated at 210° C. for 40 minutes, thus obtaining a surface-crosslinked water-absorbent resin powder (6). The water-absorbent resin powder (6) had the following properties: GVs=34 g/g; AAP4.9 kPa=25 g/g; and PPUP=50%.

Example 7

A water-absorbent resin powder (7) was obtained as in Example 1, but the acrylic acid composition (9) and the aqueous sodium acrylate solution (9) were used instead of the acrylic acid composition (2) and the aqueous sodium acrylate solution (2), respectively.

Example 8

A water-absorbent resin powder (8) was obtained as in Example 6, but the water-absorbent resin powder (2) was used instead of the water-absorbent resin powder (1). The water-absorbent resin powder (8) had the following properties: GVs=33 g/g; AAP1.9 kPa=29 g/g; AAP4.9 kPa=27 g/g; and PPUP=54%.

Example 9

A water-absorbent resin powder (9) was obtained as in Example 6, but the water-absorbent resin powder (7) was used instead of the water-absorbent resin powder (1). The water-absorbent resin powder (9) had the following properties: GVs=32 g/g; AAP1.9 kPa=28 g/g; AAP4.9 kPa=25 g/g; and PPUP=52%.

Comparative Example 4

A comparative water-absorbent resin powder (4) was obtained as in Example 1, but the acrylic acid composition (10) and the aqueous sodium acrylate solution (10) were used instead of the acrylic acid composition (2) and the aqueous sodium acrylate solution (2), respectively.

Comparative Example 5

A comparative water-absorbent resin powder (5) was obtained as in Example 1, but the aqueous sodium acrylate solution (11) were used instead of the aqueous sodium acrylate solution (1).

Comparative Example 6

A water-absorbent resin powder (6) was obtained as in Example 6, but the comparative water-absorbent resin powder (4) was used instead of the water-absorbent resin powder (1). The comparative water-absorbent resin powder (6) had the following properties: GVs=38 g/g; AAP1.9 kPa=18 g/g; AAP4.9 kPa=9 g/g; and PPUP=33%.

(Analysis Results of Water-Absorbent Resins) Table 1

Table 1 shows analysis results for the water-absorbent resin powders (1) through (5) and the comparative water-absorbent resin powders (1) through (5).

As shown in Table 1, compared to Comparative Example 1 in which a particular unpolymerizable organic compound is not used, Examples 1 through 5 and Example 7 in which a particular unpolymerizable organic compound is used, realize mildly controlled polymerization peak temperature, the shortening of the induction time, the improvement of absorption capacity (GVs), the improvement of the GEX value that indicates the relationship between absorption capacity (GVs) and water-soluble polymer, and a water-absorbent resin with no odor, and reduction in coloration (YI) of a water-absorbent resin. Further, the process of the present invention (Examples 1 through 5 and Example 7) does not have the problem of odor, unlike Comparative Examples 2 and 3.

TABLE 1

|  | Example 1 Water-absorbent resin powder 1 | Example 2 Water-absorbent resin powder 2 | Example 3 Water-absorbent resin powder 3 | Example 4 Water-absorbent resin powder 4 | Eaxmple 5 Water-absorbent resin powder 5 | Eaxmple 7 Water-absorbent resin powder 7 |
|---|---|---|---|---|---|---|
| Type of organic compounds | toluene | toluene | toluene | diphenyl ether | diphenyl ether | diphenyl |
| Solubility parameter of unpolymerizable organic compound $(Jm^{-3})^{0.5} \times 10^{-4}$ | 1.8 | 1.8 | 1.8 | 2.1 | 2.1 | 1.9 |
| Organic compound content (ppm by weight) | 10 | 100 | 1000 | 10 | 1000 | 100 |
| Temperature at start of polymerization (° C.) | 30 | 30 | 30 | 30 | 30 | 30 |
| Induction time (sec) | 85 | 85 | 85 | 85 | 85 | 85 |
| Peak time (min) | 22 | 21 | 22 | 22 | 21 | 21 |
| Peak temperature (° C.) | 77 | 78 | 78 | 76 | 76 | 78 |
| D50 (mm) | 440 | 450 | 500 | 380 | 390 | 500 |
| GVs (g/g) | 40.4 | 41.3 | 40.5 | 47.2 | 47.4 | 40.5 |
| soluble component content (%) | 10.1 | 10.7 | 10.1 | 12 | 12.1 | 10.1 |
| GEX value | 17.5 | 17.4 | 17.5 | 19.0 | 19.0 | 17.5 |
| YI value | 5 | 5 | 6 | 5 | 5 | 6 |
| Odor evaluation | 0 | 0 | 1 | 0 | 1 | 1 |

|  | Comparative Example 1 Comparative water-absorbent resin powder 1 | Comparative Example 2 Comparative water-absorbent resin powder 2 | Comparative Example 3 Comparative water-absorbent resin powder 3 | Comparative Example 4 Comparative water-absorbent resin powder 4 | Comparative Example 5 Comparative water-absorbent resin powder 5 |
|---|---|---|---|---|---|
| Type of organic compounds | — | toluene | diphenyl ether | ethyl alcohol | ethyl alcohol |
| Solubility parameter of unpolymerizable organic compound $(Jm^{-3})^{0.5} \times 10^{-4}$ | — | 1.8 | 1.7 | 2.6 | 1.8 |
| Organic compound content (ppm by weight) | — | 10000 | 10000 | 1000 | 10 |
| Temperature at start of polymerization (° C.) | 30 | 30 | 30 | 30 | 30 |
| Induction time (sec) | 90 | 90 | 130 | 130 | 250 |
| Peak time (min) | 20 | 21 | 23 | 26 | 30 |
| Peak temperature (° C.) | 82 | 76 | 77 | 75 | 72 |
| D50 (mm) | 400 | 430 | 440 | 440 | 440 |
| GVs (g/g) | 38.2 | 46.1 | 47.3 | 45 | 47.3 |
| soluble component content (%) | 10.9 | 10.1 | 13.2 | 23 | 25 |
| GEX value | 16.0 | 19.9 | 18.3 | 14.4 | 14.7 |
| YI value | 7 | 6 | 6 | 6 | 20 |
| Odor evaluation | 0 | 5 | 5 | 5 | 5 |

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention makes it possible to produce, with a high productivity, a water-absorbent resin having an improved relationship between absorption capacity and water-soluble polymer, which are conflicting properties of the water-absorbent resin, being easily controlled for polymerization reaction, being of no odor, being less colored, and being of high absorption properties.

The invention claimed is:

1. A process for producing a water-absorbent resin by polymerizing an acrylic acid composition including at least one of acrylic acid and its salt, the process comprising:
(a) the step of carrying out aqueous solution polymerization of the acrylic acid composition to form a hydrogel crosslinked polymer; and
(b) the step of drying the hydrogel crosslinked polymer by application of heat,
the acrylic acid composition having an unpolymerizable organic compound content of 1 to 1000 ppm by weight, wherein the unpolymerizable organic compound has a solubility parameter of $(1.0 \text{ to } 2.5) \times 10^4 \, (Jm^{-3})^{1/2}$.

2. The process according to claim 1, wherein:
the unpolymerizable organic compound is included or added in advance in the acrylic acid composition.

3. The process according to claim 2, wherein:
the acrylic acid composition is purified so that a content of the unpolymerizable organic compound included in the acrylic acid composition is adjusted to 1 to 1000 ppm by weight.

4. The process according to claim 1, wherein:
the unpolymerizable organic compound is at least one compound selected from the group consisting of heptane, dimethyl cyclohexane, ethyl cyclohexane, toluene, ethylbenzene, xylene, diethyl ketone, diisopropyl ketone, methyl propyl ketone, methyl isobutyl ketone, methyl-t-butyl ketone, n-propyl acetate, n-butyl acetate, diphenyl ether, and diphenyl.

5. The process according to claim 1, wherein:
the unpolymerizable organic compound is an aromatic compound.

6. The process according to claim 1, further comprising:
after the step (b), (c) the step of subjecting the hydrogel crosslinked polymer to surface-crosslinking treatment by application of heat.

7. The process according to claim 6, wherein:
in the steps (b) and (c), the heat is at a temperature not lower than a boiling point of the unpolymerizable organic compound.

8. The process according to claim 1, wherein:
in the step (b), the drying is hot-air drying with a gas having a dew point of 50 to 100° C.

9. The process according to claim 1, wherein:
the acrylic acid composition includes: methoxyphenol content of which is 10 to 200 ppm by weight; at least one compound content of which is 1 to 1000 ppm by weight, the compound being selected from the group consisting of β-hydroxypropionic acid and acrylic acid dimer; and phenothiazine content of which is 0 to 0.1 ppm by weight.

10. The process according to claim 1, wherein:
the step (a) is a step of neutralizing the acrylic acid composition with a basic composition; and then carrying out aqueous solution polymerization of a resultant neutralized product, thereby forming a hydrogel crosslinked polymer,
the basic composition including a basic compound and iron,
the basic composition having an iron content of 0.2 to 5.0 ppm by weight in terms of $Fe_2O_3$.

* * * * *